United States Patent
Podoleanu

(10) Patent No.: US 8,514,404 B2
(45) Date of Patent: Aug. 20, 2013

(54) MULTIPLE PATH INTERFEROMETER AND METHOD

(75) Inventor: Adrian Podoleanu, Canterbury (GB)

(73) Assignee: University of Kent, Canterbury, Kent (GB)

( * ) Notice: Subject to any disclaimer, the term of this patent is extended or adjusted under 35 U.S.C. 154(b) by 449 days.

(21) Appl. No.: 12/919,026

(22) PCT Filed: Feb. 24, 2009

(86) PCT No.: PCT/GB2009/050184
§ 371 (c)(1),
(2), (4) Date: Nov. 29, 2010

(87) PCT Pub. No.: WO2009/106884
PCT Pub. Date: Sep. 3, 2009

(65) Prior Publication Data
US 2011/0109911 A1 May 12, 2011

(30) Foreign Application Priority Data
Feb. 27, 2008 (GB) .................................. 0803559.4

(51) Int. Cl.
*G01B 9/02* (2006.01)
*G01B 11/02* (2006.01)
(52) U.S. Cl.
USPC .......................... 356/497; 356/479; 356/504
(58) Field of Classification Search
USPC ......................................... 356/479, 497, 504
See application file for complete search history.

(56) References Cited

U.S. PATENT DOCUMENTS

| 5,268,738 A | 12/1993 | Baney et al. |
| 5,579,112 A | 11/1996 | Sugiyama et al. |
| 6,738,144 B1 | 5/2004 | Dogariu |

(Continued)

FOREIGN PATENT DOCUMENTS

EP 1870028 A1 12/2007

OTHER PUBLICATIONS

Jonathan, "Dual arm low-coherence interferometer-based . . . ", Optics Communication, vol. 252, No. 1-3, Aug. 1, 2005, pp. 202-211.

(Continued)

*Primary Examiner* — Tari Fur Chowdhury
*Assistant Examiner* — Sunghee Y Gray
(74) *Attorney, Agent, or Firm* — Barnes & Thornburg LLP

(57) ABSTRACT

The invention discloses an optical interferometer which can be used to provide simultaneous measurements over multiple path lengths and methods to employ such an interferometer as to achieve a variety of functions covering simultaneous measurements at different depths separated by an increment of a multiple differential delay matched in the interferometer as well as imaging. Optical sensors, optical coherence tomography (OCT) set-ups, optical sensing methods and OCT methods are disclosed which can provide: (i) multiple en-face images at several depths with dynamic dispersion compensation, (ii) fast acquisition of cross sections, (iii) fast acquisition of 3D volumes of a scattering object while maintaining dynamic focus; (iv) fast acquisition of long axial measurement profiles, non mechanical, with dynamic focus, range scalable, with applications in tracking and OTDR. Methods are disclosed on the combination of scanning regimes and modes of operation to achieve versatile functionality in measurements, in the 3D imaging of moving tissue such as the eye, heart, or moving embryos or functional/low noise imaging by making use of angular compounding or polarisation. A method for elimination of axial movement effects in measuring the flow profile is also disclosed.

36 Claims, 13 Drawing Sheets

(56) References Cited

U.S. PATENT DOCUMENTS

| | | | |
|---|---|---|---|
| 6,975,781 B2 * | 12/2005 | Takiguchi et al. | 385/3 |
| 7,852,485 B2 * | 12/2010 | Alphonse et al. | 356/479 |
| 2001/0045513 A1 | 11/2001 | Kourogi et al. | |
| 2002/0003607 A1 | 1/2002 | Toida | |
| 2004/0036838 A1 | 2/2004 | Podoleanu et al. | |
| 2005/0018203 A1 | 1/2005 | Hogan | |
| 2007/0076221 A1 | 4/2007 | Toida | |

OTHER PUBLICATIONS

Motaghian, "Increased ranging depth in optical frequency . . . ", Optics Letters, Oct. 1, 2007, pp. 2768-2770.
Written Opinion in PCT/GB2009/050184.
Search Report in GB0803559.4, Jun. 27, 2008.

* cited by examiner

MULTIPLE PATH INTERFEROMETER AND METHOD

1. FIELD OF THE INVENTION

The present invention relates to an optical interferometer which can be used to provide simultaneous measurements and simultaneous optical coherence tomography (OCT) images over multiple path lengths, using principles of low coherence interferometry. Optical amplification is used to compensate for losses. The invention is applicable to time domain and frequency domain low coherence interferometry as well as to time domain and frequency domain OCT.

2. BACKGROUND OF THE INVENTION

In the description which follows, reference is made primarily to the eye. This has to be understood as merely a way to help the description and not as a restriction of the application of the present invention. As such, where the term "eye" is used, a more general transparent and scattering object or organ may be sought instead, the invention could equally be applied to skin, heart, vessels, embryos, dental tissue, dental prostheses, paintings, powders and other scattering semi-transparent objects.

3. DESCRIPTION OF THE PRIOR ART

Low coherence interferometry is an absolute measurement technique which allows high resolution ranging and characterization of optoelectronic components. The potential of the technique for high resolution imaging of the tissue is often referred to as optical coherence tomography (OCT) as presented in D. Huang, E. A. Swanson, C. P. Lin, J. S. Schuman, W. G. Stinson, W. Chang, M. R. Hee, T. Flotte, K. Gregory, C. A. Puliafito and J. G. Fujimoto, 'Optical coherence tomography', *Science* 254, pp. 1178-1181, 1991.

Different scanning procedures are explained in the patent application US20030199769A1. A-scans are axial reflectivity profiles and B-scan images are obtained by grouping together several A-scans for adjacent transverse position of the scanning beam.

OCT has also been reported as being capable of providing en-face, or transversal profiles, or T-scans, which are reflectivity profiles generated by moving the beam transversally across the target. Based on T-scans, constant depth images (C-scan, or images with the same orientation as in microscopy) can be generated, as reported in "Coherence Imaging by Use of a Newton Rings Sampling Function" by A. Gh. Podoleanu, G. M. Dobre, D. J. Webb, D. A. Jackson, published in Opt. Lett., Vol. 21, No. 21, (1996), pp. 1789-1791 and in "Transversal and Longitudinal Images from the Retina of the Living Eye Using Low Coherence Reflectometry", by A. Gh. Podoleanu, Mauritius Seeger, George M. Dobre, David J. Webb, David A. Jackson and F. Fitzke, published in the Journal of Biomedical Optics, 3(1), pp. 12-20, 1998. T-scan technology is also described in the U.S. Pat. No. 5,975,697.

All the documents above refer to time domain (TD)-OCT methods. Higher acquisition speed OCT methods use spectral domain (SD)-OCT. However, such methods are not compatible with dynamic focus. This means that the sensitivity varies across the depth range, especially detrimental when the depth range is wide. Also, in spectral OCT, high numerical aperture microscope objectives cannot be used.

Time domain OCT however is compatible with dynamic focus. If the acquisition rate of time domain can be increased to the level of SD OCT, maintaining good signal to noise ratio, then better quality images can be obtained using time domain OCT under dynamic focus, in a length of time similar to that required by SD-OCT.

In terms of line rate, TD-OCT could reach fast line scanning rates using resonant scanners (16 kHz). This is 2-7 times less than the scanning rate of modern line scan cameras used in channeled spectrum (CS)-OCT and more than an order of magnitude smaller than the rate achievable using swept source (SS)-OCT, which are the two versions of SD-OCT, now very popular. It looks unlikely that the line rate in en-face OCT can be further increased. However, for any given line rate, en-face OCT has an unexploited potential in the possibility of simultaneous acquisition of several C-scan images from different depths, on the expense of power division in the reference path, where power is normally attenuated to reduce the noise.

In order to speed up the acquisition of TD-OCT methods, several methods and devices have been proposed in prior art to provide imaging at different depths simultaneously. Procedures of dividing the power in the reference path of the interferometer have been explored in prior reports. Two OCT channels have been demonstrated using a two splitter configuration, as presented in the article "Simultaneous en-face imaging of two layers in the human retina by low-coherence reflectometry", by Podoleanu, A. G., Dobre, G. M., Webb, D. J., Jackson, D. A., published in Optics Letters 22, 1039-1041, 1997. A different configuration employed an integrated Mach-Zehnder modulator, where two delays have been introduced in the reference arm, each with its own RF modulation, as described in the article "Simultaneous low coherence interferometry imaging at two depths using an integrated optic modulator", by Podoleanu, A. Gh., Rogers, J. A., Cucu, R. C., Jackson, D. A., Wacogne, B., Porte, H., Gharbi, T., published in Optics Communications 191, 21-30, 2001. The frequency modulation limit of the first solution and the dispersion of the modulator of the second solution rendered these approaches unsuitable for in-vivo applications.

Another possibility is to split both the object and reference arms as presented in the "Hybrid configuration for simultaneous en-face OCT imaging at different depths", by Podoleanu, A. Gh., Cucu, R. G., Pedro, J., Weitz, R., Jackson, D. A., Rosen, R. B., in SPIE Conference Proc. 5634, 160-165, 2004b and in the U.S. Pat. No. 6,927,860B2. In this way, two independent OCT imaging channels are assembled. However, such a configuration cannot be extended to a larger number of channels due to the complexity of splitting the two optical beams, object and reference, as well as due to the losses introduced by such splitting. Such configuration has also the disadvantage that a photodetector unit is required for each channel.

A low coherence interferometer was disclosed in the U.S. Pat. No. 5,268,738 where a recirculating loop equipped with a frequency modulator is used to extend the range of measurement of the device, with applications in sensing. In this way, multiple depths can be interrogated, separated by the length of the recirculating loop and a distinction can be made between different paths based on the frequency shift acquired by the wave in the loop for each round trip. However, the recirculating loop is much longer than the coherence length of the optical source, and the loop is used in this patent for extending the range of measurements. If delays shorter than the coherence lengths are required, the solution provided does not work, as the modulator itself and fibre launchers only are longer than cm length. If multiple sensors need to be interrogated situated at distances comparable with the coherence length, then the loop has to be made of very small length which is not practical.

A solution to provide multiple coherence signals from axial distances, whose differences are comparable with the coherence length of the source is disclosed in the patent application US 2003/0025913, by J. A. Izatt and A. M. Rollins where combination of passive Mach Zehnder modulators ensure several multiple delays. The disclosure restricts the application of such trees of modulators to the reference arm of the interferometer, where the optical power needs to be attenuated to reduce the noise. This solution is not applicable to the object arm, where signal is weak, as the tree of Mach Zehnder modulators is lossy. As another disadvantage, the differential delay between successive axial positions cannot be changed and is given by the length of the Mach Zehnder modulators. As another disadvantage, they all need to have similar differential delay, which may be difficult to implement in practice, unless high manufacturing precision is ensured, which may lead to high manufacturing cost.

The configurations disclosed in the two prior art documents above do not admit reconfiguration in order to allow measurements from different variable axial positions. As another disadvantage, it is not possible to put all channels together, i.e. to sum up all channels to collect light from the same depth, or from depths slightly different, but smaller than the coherence length as required by different regimes of operation in the OCT practice. Such versatility may be important in the speckle reduction, in generating en-face images with adjustable depth resolution using OCT, in generating a scanning laser ophthalmoscopy (SLO)-like image by providing a summed OCT image collected from several depths which cover the whole retina depth, or in polarization sensitive imaging.

In terms of speckle reduction, the applications WO2004/088361 (Tearney et al) describes a solution for angular compounding using a microscope slide plate, however this is applicable to longitudinal OCT images only, the images are not obtained simultaneously and the solution disclosed is not reconfigurable.

Swept source OCT is fast, however has the principle disadvantage that the depth is limited by the optical source linewidth of the tunable laser. A large depth of range of cm is not feasible due to relatively wide line-width achieved to date which is larger than 0.1 nm. In contrast, time domain OCT can cover any depth range. It would be therefore advantageous to devise a method to generate swept source OCT images from several sub depth intervals to the extent allowed by the linewidth and then synthesise the large depth B-scan image. However, if such a solution seems feasible by repeating acquisition for different reference depth positions over sub-intervals of the depth range, this takes time.

Therefore, the present invention seeks to overcome the above disadvantages, providing configurations and methods of operation, characterized by parallel or fast sequential acquisition, low loss and an easily controllable differential delay which may be made available at reasonable cost and which have stability, ease of operation, with increased versatility in comparison with existing implementations, allowing reconfiguration, adjustment of the value of multiple OPD values and implementation of different regimes of operation as well as different types of OCT scanning, T-scan, B-scan or C-scan.

4. SUMMARY OF THE INVENTION

In a first aspect, the present invention relates to an interferometer where re-circulating paths are provided in both arms of the interferometer and multiple channel receivers, each sensitive to one value of the optical path difference only, are fed using only one photo detection unit.

In a second aspect, the invention provides means for adjustment of the positions in depths, or the axial distances where signal is collected from, independent in the range value and in the differential distance between successive such points.

In a third aspect, the present invention provides means for adjustment of the differential delay between successive points in depths, or axial distances, allowing that all channels sense the same axial distance, or in OCT, all channels collect images from the same depth. Solutions are provided to adjust the differential delay to very small values, much less than the coherence length of the partial coherent light source, or larger than the coherence length.

In a fourth aspect, the loss of previous configurations is eliminated by providing active multiple paths, where optical amplifiers amplify the signal and compensate for the round trip loss in recirculating loops.

In a fifth aspect, the present invention sets out a method for speeding up the acquisition of B-scan OCT images and C-scan OCT images compatible with dynamic focus.

In a sixth aspect, the invention provides a method for producing an en-face (C-scan) OCT image, similar to that delivered by a scanning laser ophthalmoscope or a conventional microscope in one instant frame, to provide guidance to the high resolution imaging process, i.e. a thick C-scan image, with a thickness similar to that of the depth range of the imaging instrument.

In a seventh aspect, the invention provides a method for producing the depth profile inside a vessel, less affected by the movement of the tissue or vessel support.

In an eighth aspect, the invention provides a method for producing simultaneously polarization sensitive measurements.

In a ninth aspect, the invention provides means and a method for despeckle of the OCT image by angular compounding.

In a tenth aspect, the invention provides a method for fast shifting interferometry, with simultaneous collection of different phases of the optical signal from the object. This can be used in the process of demodulation to provide amplitude and phase by using at least three recirculating waves in the multiple path interferometer, or can be used to reduce the speckle.

In an eleventh aspect, the invention provides a method for acquisition of a 3D volume by acquiring several C-scan images from different depths at the same time, in a time required for acquiring one C-scan image.

In a twelfth aspect the invention provides a method for acquiring A scans and B-scans using swept source OCT where the depth range of A-scans or B-scans widely exceeds the maximum depth range given by the source linewidth.

In a thirteenth aspect, the invention provides a method for automatic dispersion compensation while scanning in depth, applicable to both time domain and spectral domain OCT.

In a fourteenth aspect, the invention provides means for instantaneous demultiplexing of several sensors applicable to both time domain and spectral domain low coherence interferometry.

In a fifteenth aspect, the invention provides fast optical time domain reflectometry (OTDR) scans, or fast A-scans in OCT, compatible with dynamic focus.

In a sixteenth aspect, the invention provides means for molecular recognition by amplifying either small changes in optical delays or small changes in frequency shifts of the output optical signal traversing a biological sample or a drug which are compared with respectively changes in the optical delay or changes in the frequency shifts of a reference sample.

5. BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which:

FIG. 5b illustrates the overall depth range achieved with the embodiment in FIG. 5a.

Figure 6A:
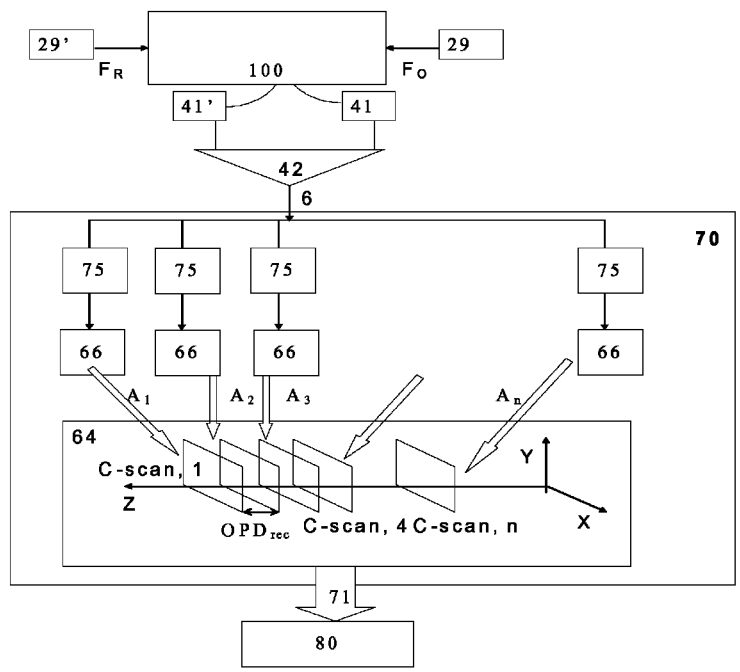
Figure 6B:
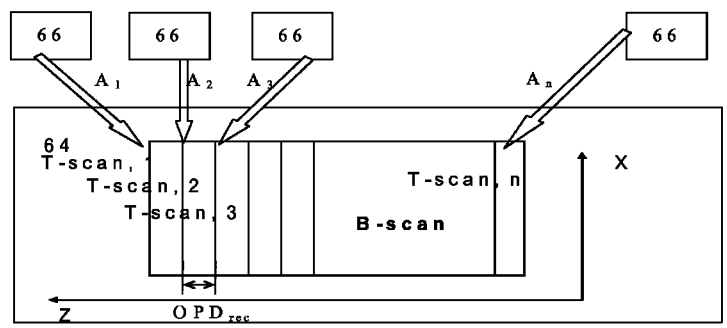

FIGS. 6a and 6b present embodiments of the demodulator block which provide simultaneously multiple interference signals from different optical path difference (OPD) values.

Figure 7:
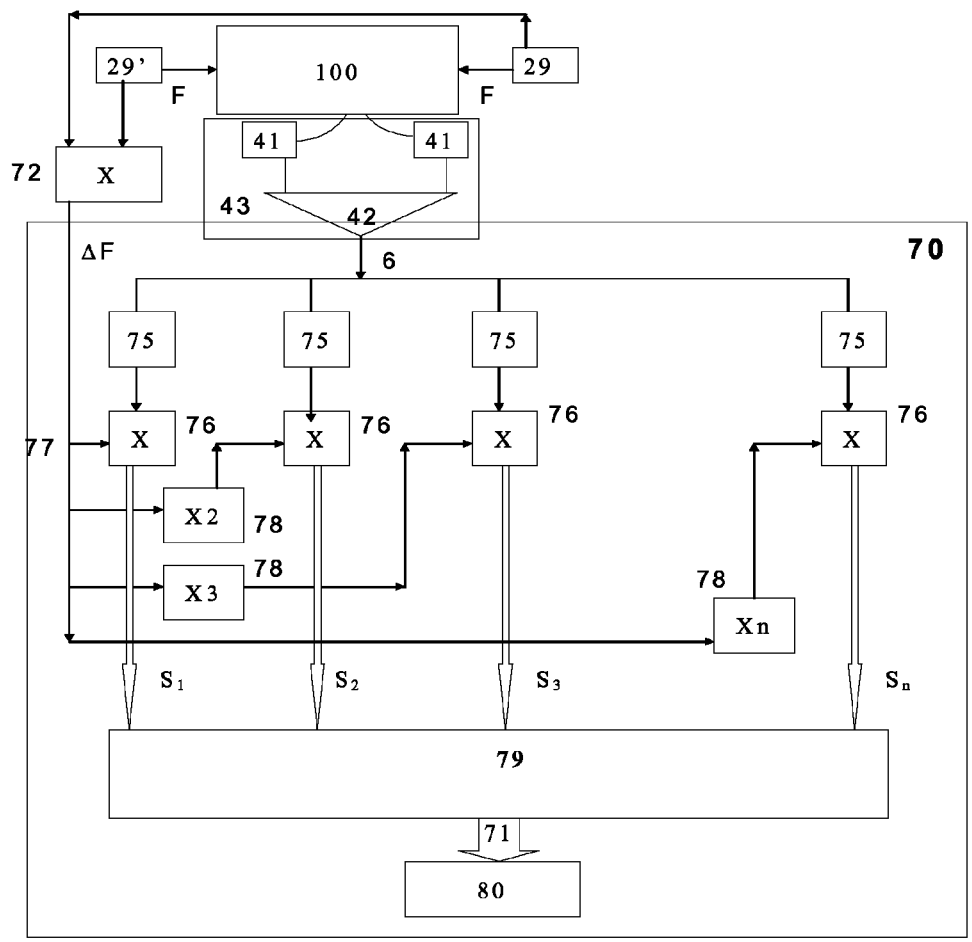

FIG. 7 presents a second embodiment of the demodulator block which performs phase shifting interferometry.

Figure 8:
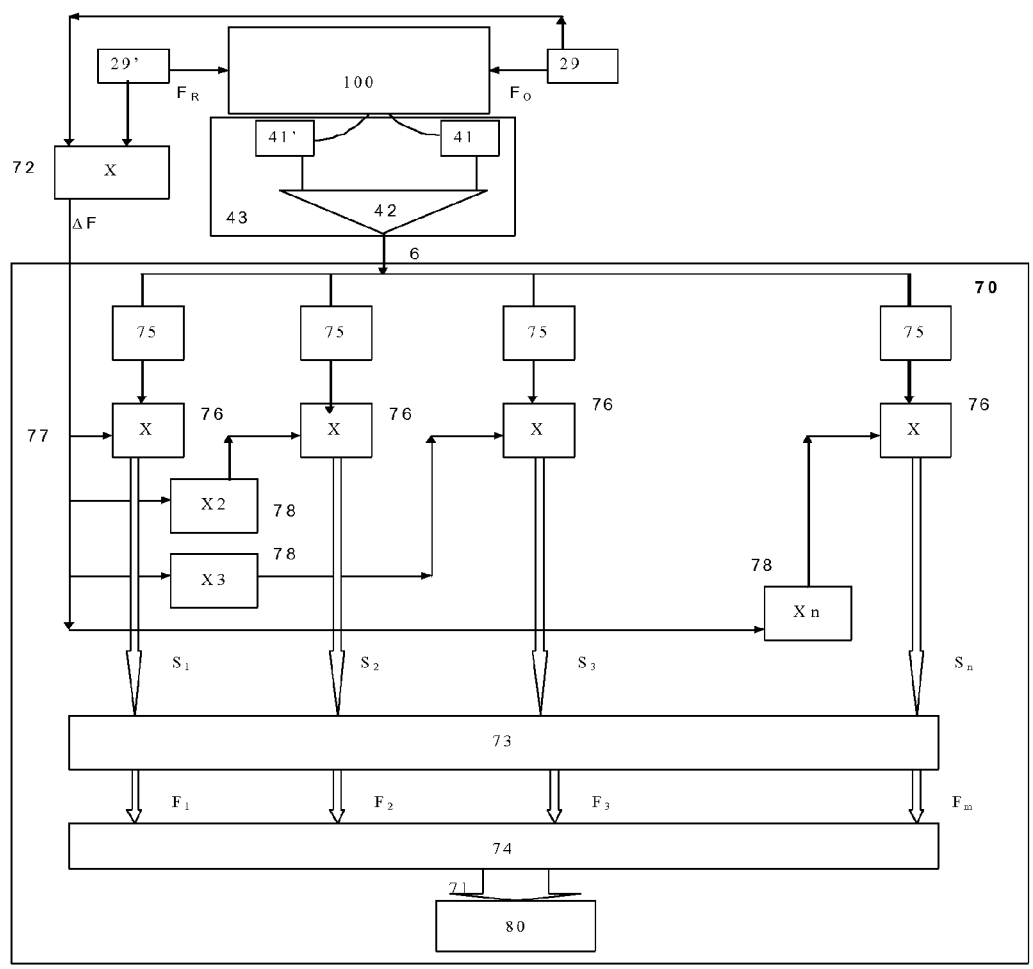

FIG. 8 presents a third embodiment of the demodulator block which provides flow measurement and imaging while subtracting the axial movement of the object.

Figure 9:
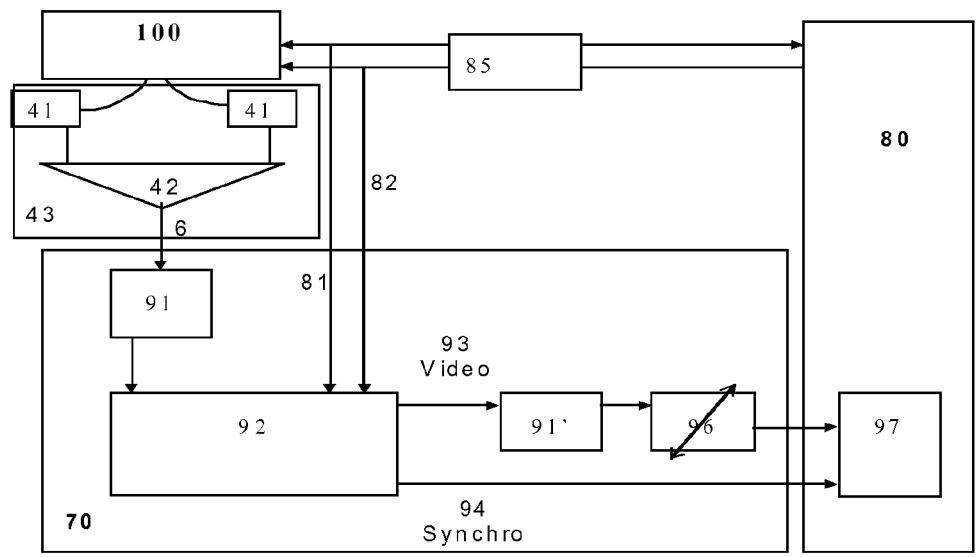

FIG. 9 presents a fourth embodiment of the demodulator block which provides storage of volume information which allows subsequent selection of slices at any depth inside the stored volume.

Figure 4:
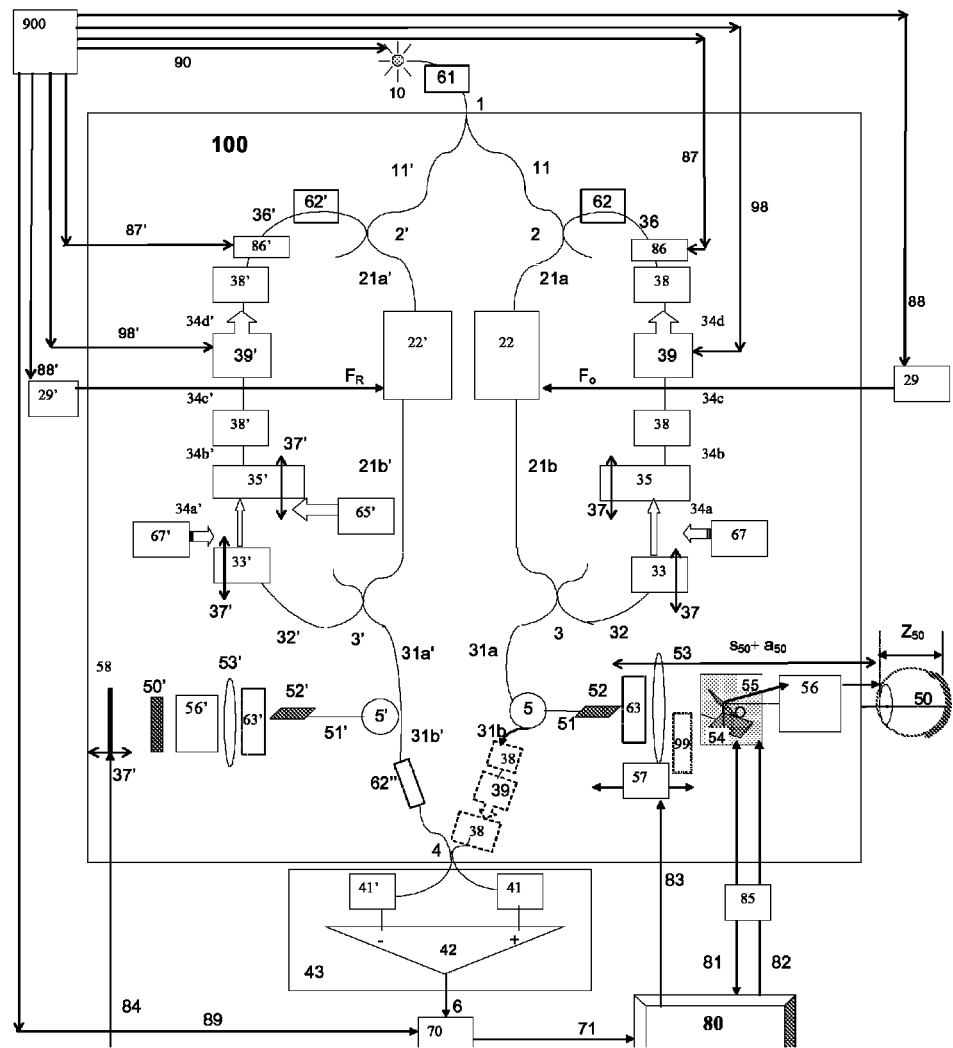
FIG. 4 shows an embodiment of the present invention which performs imaging.
Figure 10A:
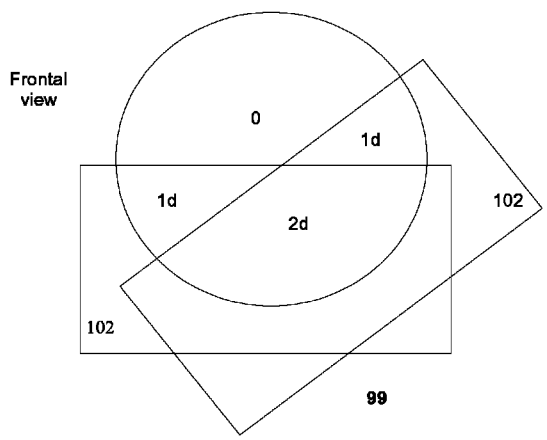
Figure 10B:
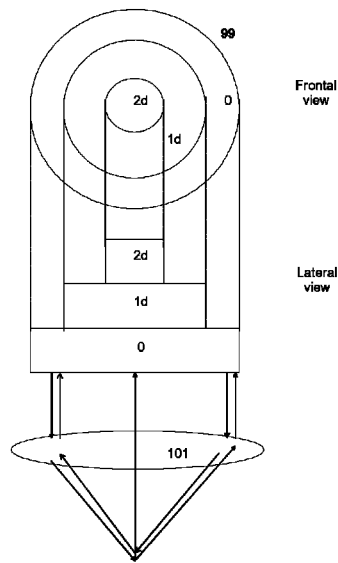

FIGS. 10a and 10b present two possible embodiments of optical delay elements which in conjunction with the embodiment in FIG. 4 can provide angular compounding.

Figure 11:
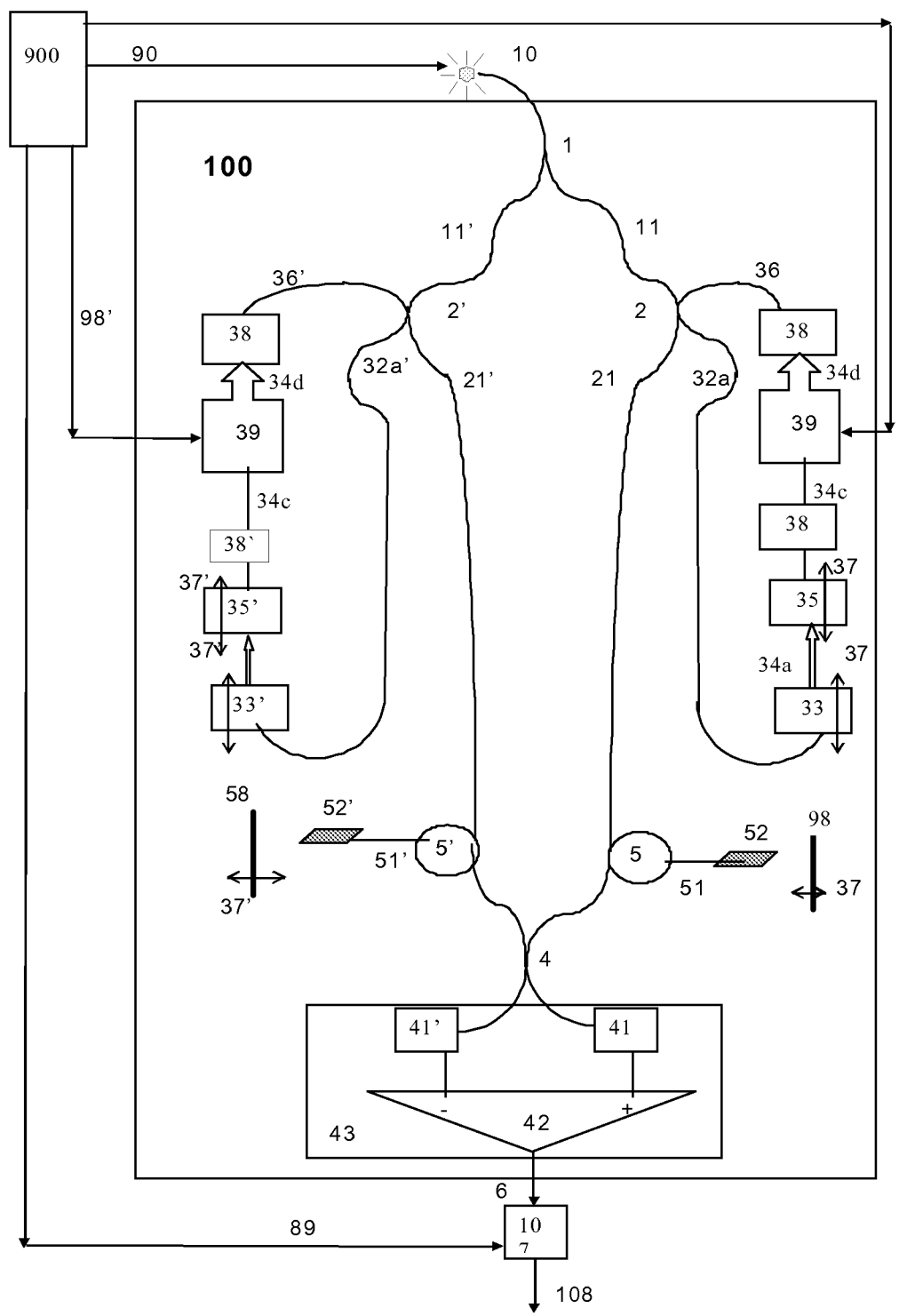

FIG. 11 discloses a configuration which operates on single pulse and no frequency shifting.

Figure 12A:
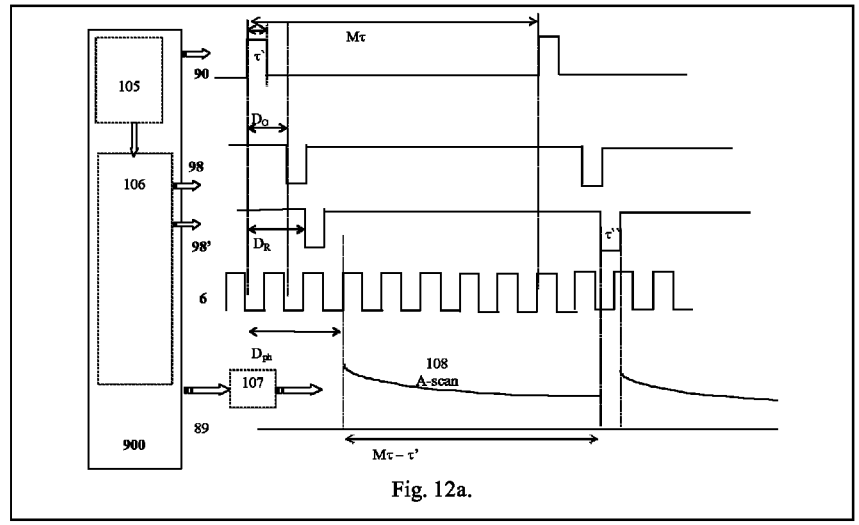

FIG. 12a describes the principle of operation of the embodiment in FIG. 10 and shows the time diagram of controlling pulsed signals necessary to achieve a fast A-scan.

Figure 12B:
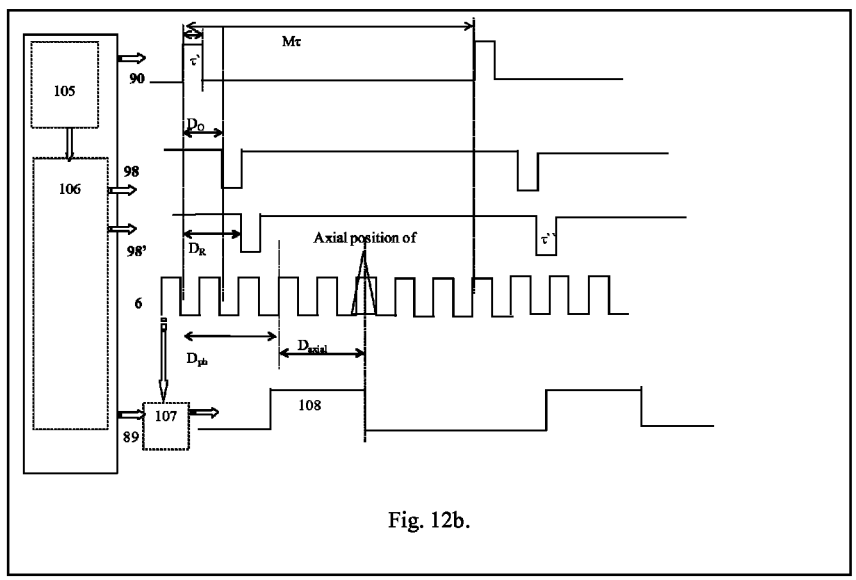

FIG. 12b describes the principle of operation of the embodiment in FIG. 10 and shows the time diagram of controlling pulsed signals necessary to achieve fast tracking operation.

Figure 13A:
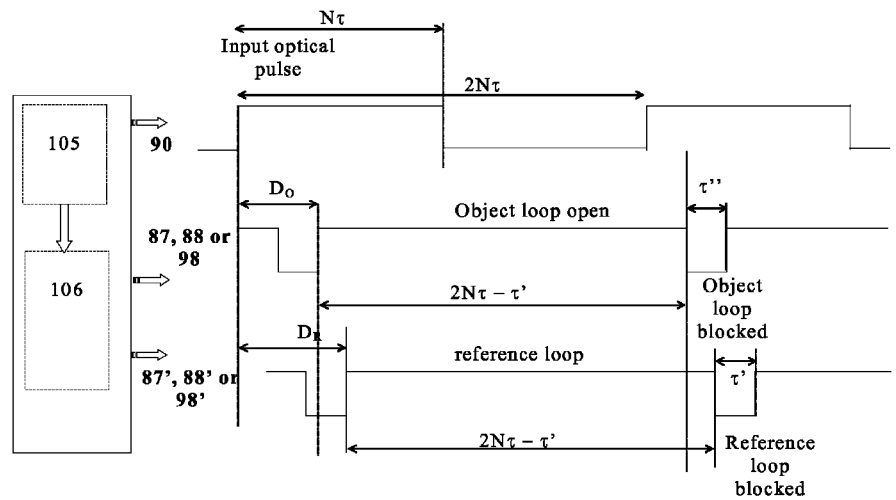
Figure 13B:
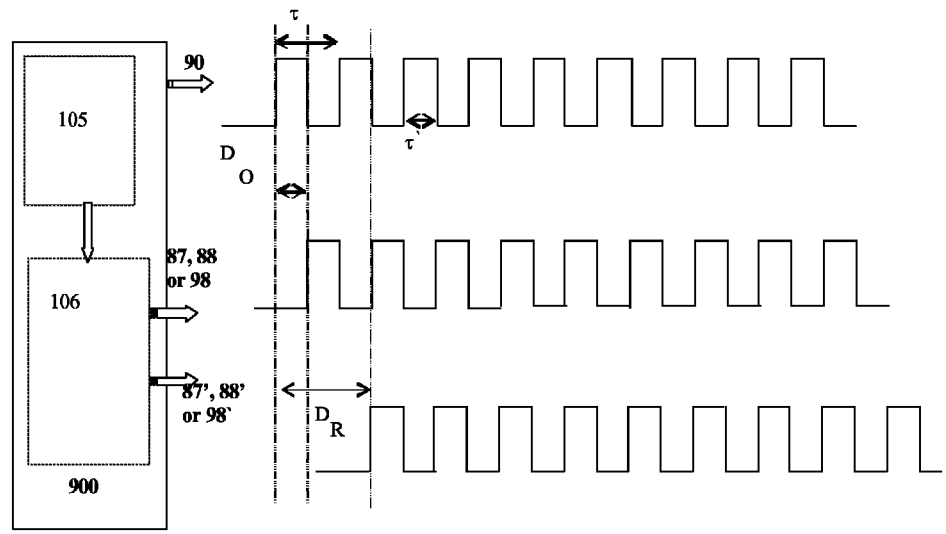

FIGS. 13a and 13b illustrate different timing of signals controlling the embodiments in FIGS. 1-4.

6. DETAILED DESCRIPTION OF THE PREFERRED EMBODIMENTS

Various features of the present invention, as well as other objects and advantages attendant thereto, are set forth in the following description and the accompanying drawings in which like reference numerals depict like elements.

All lengths below are optical, they include the index of refraction of the fibre link or air or of the object.

Figure 1:
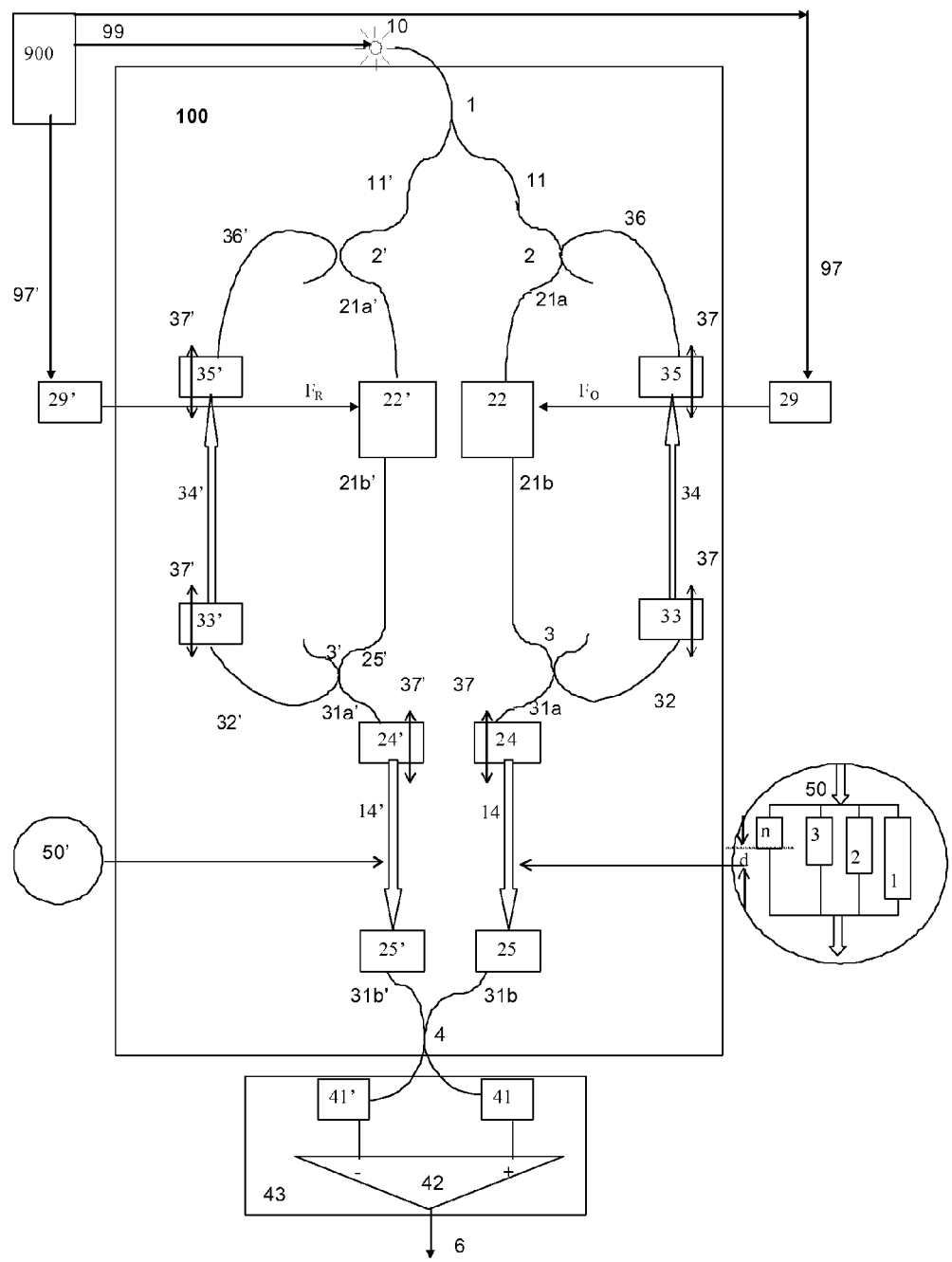
FIG. 1 shows, in diagrammatic form, the main elements of the multiple path recirculating interferometer according to a first embodiment.

FIG. 1 shows, in diagrammatic form, the main elements of the multipath recirculating interferometer 100, here light from an optical source, 10, is divided into two beams, object and reference, at the output of a first splitter, 1, wherefrom light from one of its output feeds the main object path formed from path 11, of optical length $s_{11}$, towards a $2^{nd}$ splitter, 2, via another part of the main object path, 21a, of length $d_{21a}$, towards an object modulator 22, which can be a frequency shifter or a phase modulator, of optical path length, $d_{22}$, modulated at a frequency $F_O$, along path 21b, of length $d_{21b}$, towards the $3^{rd}$ object splitter, 3, where the first of its output feeds beam along path 31a of the object path, of length, $s_{31a}$, towards a connector and collimator 24 of length $s_{24}$, via an air path $a_{14}$ towards a collimator and connector 25 of length $s_{25}$ connected to the first input of a 4th main splitter, 4 via a fibre of length $s_{31b}$, where the splitter 4 is terminated on a photodetecting unit, 43. This is made from two photodetectors, 41 and 41' and a differential amplifier, 42. The optical path length of the main object path from the $1^{st}$ main splitter, 1, till the $4^{th}$ main splitter, 4, is of length:

$$D_O = s_{11} + d_{21a} + d_{21b} + d_{22} + s_{31a} + s_{31b} + s_{24} + s_{25} + a_{14} \quad (1)$$

The main reference path starts at the other output of the first splitter, 1, along path 11', of length $s_{11'}$, towards a $2^{nd}$ splitter, 2', via another part of the main reference path, 21', of length $d_{21a'}$, towards a reference optical modulator, 22', which can be a frequency shifter or a phase modulator, of optical path length, $d_{22'}$, modulated at a frequency $F_R$, along path 21b' of length $d_{21b'}$, towards the $3^{rd}$ reference splitter 3', where the first of its output feeds beam along path 31a' of the reference path, of length, $s_{31a'}$, towards a connector and collimator 24' of length $s_{24'}$, via an air path $a_{14'}$ towards a collimator and connector 25' of length $s_{25'}$ connected to the $2^{nd}$ input of the 4th splitter, 4 via a fibre of length $s_{31b'}$.

The optical path length of the main reference path from the $1^{st}$ main splitter, 1, till the $4^{th}$ main splitter, 4, is of length:

$$D_R = s_{11'} + d_{21a'} + d_{21b'} + d_{22'} + s_{31a'} + s_{31b'} + s_{24'} + s_{25'} + a_{14'} \quad (2)$$

The dispersion compensation in the main loop, for low coherence gating, requires that:

$$s_{11} + d_{21a} + d_{21b} + d_{22} + s_{31a} + s_{31b} + s_{24} + s_{25} = s_{11'} + d_{21a'} + d_{21b'} + d_{22'} + s_{31a'} + s_{31b'} + s_{24'} + s_{25'} \quad (3a)$$

and $$a_{14} = a_{14'} \quad (3b)$$

where adjustment of the main OPD is via the air path lengths $a_{14}$ and $a_{14'}$. This is performed by actuating on the launchers 24 and 24' which allow adjustment of the optical path length in the main loop along the main object path length, $D_O$ and along the main reference path length $D_R$, this can be achieved via translation stages, the arrows 37 and 37' signify means for axial movement. Finally, they allow adjustment of the OPD in the main loop, $OPD_{main}$:

$$OPD_{main} = \Delta D = D_O - D_R \quad (4)$$

by altering the path lengths in air: $a_{14}$, or $a_{14'}$ or both. Equivalently, air path could be included along paths 21a (21a'), 21b (21b') or both and launchers can be used to launch light in air along adjustable path lengths. If the optical modulators 22 and 22' are in bulk, then the inputs of the coupler 3 and 3' could be equipped with axially moving launchers.

At its 2nd output, via path 32, of optical path length, $l_{32}$, the $3^{rd}$ object splitter, 3, launches a recirculating beam via launcher 33, of optical path length, $l_{33}$, along an air path 34 of path length, $a_{34}$, towards launcher 35, of optical path length, $l_{35}$, towards the second input of the $2^{nd}$ object splitter, 2, along path 36, of optical path length, $l_{36}$, where light is reinjected back into the main object path, starting with path 21a.

The path length of the recirculating object loop from the $3^{rd}$ object splitter, 3, via the second input of the $2^{nd}$ object splitter, 2, and via the optical modulator, 22, is:

$$L_O = l_{32} + l_{33} + a_{34} + l_{35} + l_{36} + d_{21a} + d_{21b} + d_{22} \quad (5)$$

At its 2nd output, via path 32', of optical path length, $l_{32'}$, the $3^{rd}$ object splitter, 3', launches a recirculating beam via launcher 33', of optical path length, $l_{33'}$, along an air path 34' of path length, $a_{34'}$, towards launcher 35', of optical path length, $l_{35'}$, towards the second input of the $2^{nd}$ object splitter, 2', along path 36', of optical path length, $l_{36'}$, where light is reinjected back into the main reference path, starting with path 21a'. The path length of the recirculating reference loop from the $3^{rd}$ reference splitter, 3', via the second input of the $2^{nd}$ reference splitter, 2', and the frequency optical modulator, 22', is $$L_R = l_{32'} + l_{33'} + a_{34'} + l_{35'} + l_{36'} + d_{21a'} + d_{21b'} + d_{22'} \quad (6)$$

The launchers 33 and 33' (along with launchers 35 and 35') allow adjustment of the optical path length in the recirculating loops, along the recirculating object path length, $L_O$ and along the recirculating reference path length $L_R$, as shown by arrows 37 and respectively, 37', by altering the lengths of air paths $a_{34}$, or $a_{34'}$ or both. Finally, they allow adjustment of the OPD between recirculated optical waves in the recirculating loops, of $OPD_{rec}$.

What is important according to the invention is that means are provided to adjust the $OPD_{main}$ independent to the value of the recirculating OPD, $OPD_{rec}$:

$$OPD_{rec} = \Delta L = L_O - L_R \quad (7)$$

(as well as its multiples, $2\Delta L, 3\Delta L, \ldots m\Delta L$, etc.). Dispersion compensation for coherence gating, when $OPD_{rec} = 0$ requires that:

$$l_{32} + l_{33} + l_{35} + l_{36} + d_{21a} + d_{21b} + d_{22} = l_{32'} + l_{33'} + l_{35'} + l_{36'} + d_{21a'} + d_{21b'} + d_{22'} \quad (8a)$$

and $$a_{34} = a_{34'} \quad (8b)$$

By adjusting the lengths of paths $a_{34}$ and $a_{34'}$, $OPD_{rec}$ is adjusted only. Preferably, the coherence position is adjusted first in the main loop actuating on the lengths $a_{14}$ and $a_{14'}$ and then the recirculating loop OPD is adjusted actuating on 37 and 37' to alter $a_{34}$ and $a_{34'}$.

The photodected signals from photodetectors 41 and 41' are sent to a differential amplifier 42 which outputs the interference signal 6 and performs balance detection. The splitter 4 is therefore preferably a 50/50 single mode coupler or a bulk beam-splitter.

Obviously, the photodetecting unit 43 can consist in a single photodetector, 41, or 41' and balance detection may not be necessary, especially in sensing where the signal is sufficiently strong.

The optical modulators 22 and 22' are driven by drivers 29 and 29' respectively. If acousto-optic modulators (AOM) are used as Bragg cells, either in bulk or in fibre, they operate as frequency shifters, at $F_O$, $F_R = 40$, 80 or 160 MHz. Depending on the bandwidth of the measurement signal, in case the interferometer in FIG. 1 is used in sensing, or depending on the image bandwidth, in case the interferometer in FIG. 1 is used in OCT imaging, the difference of frequencies:

$$\Delta F = |F_O - F_R| \quad (9)$$

defines an interference frequency shift and has to be larger than the sensing or image bandwidth respectively. For instance, for applications in sensing, $\Delta F$, could be kHz or tens of kHz. For fast OCT imaging, the bandwidth is larger than 100 kHz, in which case $\Delta F$ has to be larger than a few hundred of kHz. In some applications, it may be desirable to adjust $\Delta F$ to zero or eliminate 22 and 22' altogether and connecting 21a to 21b (respectively 21a' and 21b').

It is equally possible to use a frequency shifter which shifts the frequency up and the other down, in which case:

$$\Delta F = F_O + F_R \quad (9a)$$

This may be desirable in those circumstances where a large carrier frequency of the photodetected signal is required, such as tens of MHz to 1 GHz. These are achievable using current technology, as AOM frequency shifters operating at over 300 MHz already exists.

If the optical modulators are phase modulators, then the drivers are DC power supply which imprint a certain phase modulation, or rotation of polarisation.

It should be also obvious for those skilled in the art that one optical modulator (phase or frequency shifter) 22 or 22' only could be used with similar results. The utilization of two optical modulators is preferred for dispersion reasons as well as allowing the photodetector unit 43 work on lower frequency values (applicable when using frequency shifters).

It should also be possible to insert the optical modulators in the recirculating loop part outside the main path part in FIG. 1. In this case, the main loop provides signal in the base band while the recirculating loops provide signal around multiple of the interference frequency shift, $m\Delta F$.

6.1. Sensing

The inset in FIG. 1 illustrates a sensing application of the multipath interferometer. Along the path 14, a sensor 50 is interleaved. One example of such sensor is equipped with multiple sensing paths, $m=1$ to $n$, of optical path lengths $z_1, \ldots z_n$, differing by an increment, d. The sensors on each path may be vibrators at different frequencies, $f_1, \ldots f_n$. They modulate the waves on each path either in amplitude or in phase or in frequency. An equivalent sensor can be devised in reflection, where each sensing path ends with a mirror and the injection of the tree in the inset is via a circulator or a splitter, as shown in FIG. 4. The sensing paths, either in reflection or transmission exhibit delays in steps d, larger than half of the value of the coherence length of the source 10. Then $\Delta L = OPD_{rec}$ is adjusted to match d, and if $D_o$ is measured along the longest sensing path, $z_1$ in the inset in FIG. 1, length which matches $D_R$, then subsequent recirculations will match shorter lengths, $z_m$. In this way the amplitude and phase of the beam in the sensing path m is coded on a carrier $m\Delta F$.

The sensor could operate based on the alteration of its individual path lengths or of its attenuations. The multiple sensing paths can be used for instance for biochemical analysis, for measurement of the index of refraction of different constituents, or of their absorption, where drops of drugs placed on the sensing paths act as absorbers or refractors and change the intensity and delay of the light propagating along that path.

If the drops investigated placed on the sensing paths $z_1, \ldots z_n$, or the sensing action to be evaluated alter the value of the delays $z_m$, then this could be sensed in two ways, based on principles of coherence gating. When the source 10 is low coherence, then by scanning the $OPD_{main}$, the different OPD values of the sensing paths are matched by coherence gating with the $OPD_{rec}$. Alternatively, the optical source is a coherent tuning source and using principles of swept source low coherence interferometry, the multiple OPD values due to the recirculating paths and due to the sensor are simultaneously scanned along an axial distance determined by the source linewidth.

For dispersion compensation, a "dummy" sensor track is placed in the reference path 14'. This could be simple track, or multiple track similar to the sensor 50'.

Instead of multiple paths, the sensor 50 could also be made from a single sensing track. In this case, the sensor is placed in the object recirculation path 34 non shared with the main object path. For dispersion compensation or for needs of more sensitive comparison, a "dummy" sensor is placed in the reference recirculation path non shared with the main reference path. The multiple round trips act as amplification of two possible effects.

6.2. Differential OPD Amplification

The embodiment in FIG. 1 can operate with two identical path sensors placed in the two recirculating arms. Then, a drop of an analyte is placed on one of them. The change in the OPD due to the drop may be insignificant in single path. Let us say that due to the drop, the OPD of the sensing path changes by 0.1 micron. In 100 round trips, the differential delay is enhanced to 10 microns. This can be found by scanning the $OPD_{main}$ by using one of the launchers 24 or 24' until we recover coherence gating. In this way, the multiple round trips magnify the tiny differential delay. In this case, the frequency shifters 22 and 22' may not be necessary. They could either be driven by the same frequency or simply they could be removed from the path 21(21').

6.3. Frequency Shift Amplification

Let us say that the analyte to be identified is placed in one object cuvette, within the air path of the object, 34, filled initially with a neutral liquid, the same as in a reference cuvette placed in the reference recirculating path, 34'. Let us say that the analyte determines a small frequency shift, $\delta F=10$ Hz. This is hard to be quantified at optical frequencies. However, by taking advantage of the embodiment in FIG. 1, at each round trip, the frequency is shifted by $\delta F$. After N=100 passes, the frequency shifts by 1 kHz, which is much easier measured, using a spectrum analyzer to which the signal 6 is sent to. In this case, the optical source to be used may preferably have narrow linewidth.

The analyte may produce a Raman shift, where the shift is within the secondary loop bandwidth. Alternatively, the sensor is a surface enhanced Raman sensor (SER) and two such sensors are placed in the two recirculating paths.

Alternatively, the two sensors 50 and 50', either one track or SERs are used for molecular identification of a chemical compound. When similar compounds are used, a zero shift results. Different substances can in this way be identified, or matched with a reference substance. The narrower the spectrum of the photodetected signal 6, the closer the two substances are.

The frequency shift may also be determined by simple scattering. It is known that by scattering, frequency is also shifted. This was very hard to measure so far, as the shift is small. The embodiment in FIG. 1 allows such measurement due to its capability to amplify the frequency deviation in relation to a similar sample. The embodiment gives the possibility to compare scattering from two similar cells, by amplifying their tiny frequency shifts.

The two devices, 50 and 50', which can be compared and used in the embodiment in FIG. 1 to amplify differences of parameters could be diverse. For instance, the sensors could be microfluidic devices, where proteins or microorganism are forced to flow through tiny spaces. The frequency shift due to the flow in two such devices can be compared, one subject to a drug which influences the metabolism of the sample investigated.

Figure 2:
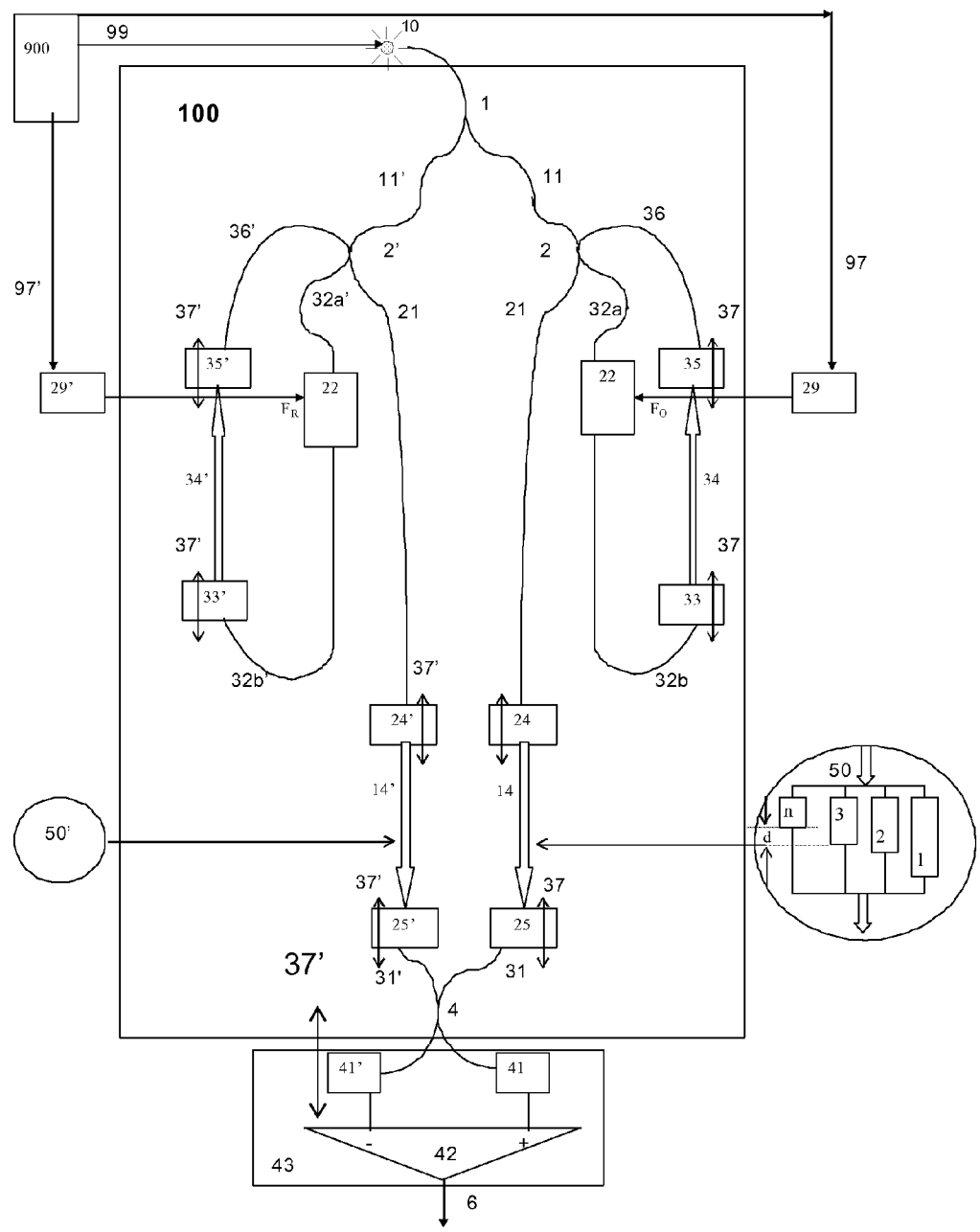
FIG. 2 shows a second embodiment of the invention.

A second embodiment is shown in FIG. 2. The splitters 3 and 3' are eliminated and the paths 32 and 32' consist of two paths, 32a and 32b, respectively 32a' and 32b'. The equations 3a and 8a become respectively:

$$s_{11}+d_{21}+s_{24}+s_{25}=s_{11'}+d_{21'}+s_{24'}+s_{25'} \tag{3a'}$$

$$l_{32a}+l_{32b}+l_{33}+l_{35}+l_{36}+d_{22}=l_{32a'}+l_{32b'}+l_{33'}+l_{35'}+l_{36'}+d_{22'} \tag{8a'}$$

while equations 3b and 8b still hold.

This embodiment has advantages in terms of losses in the recirculating paths, as only one splitter, 2(2') is used and not two as in FIG. 1. There is also no shared path between the recirculating path and the main path, apart from the splitting region in splitter 2(2').

In terms of losses, let us consider that the splitters 2 and 3 (as well as 2' and 3') are 50/50 in FIG. 1. For each round trip in each of the recirculating loop, reference or object, the power is reduced by at least a factor of ¼. The interference signal is proportional to the square root of the product of the object and reference powers, and therefore it will also reduce by a factor of ¼.

To reduce the losses in the recirculating loops, the splitting ratio of the splitters 2 and 3 (as well as 2' and 3') can be set to a higher transmission in the cross state, for instance 10/90 splitters will lead to reduction from round trip to the next of the interference signal by only $0.9^2=0.81$. However, as the number of passes increases, less and less power is obtained in each recirculating replica beam.

Figure 3:
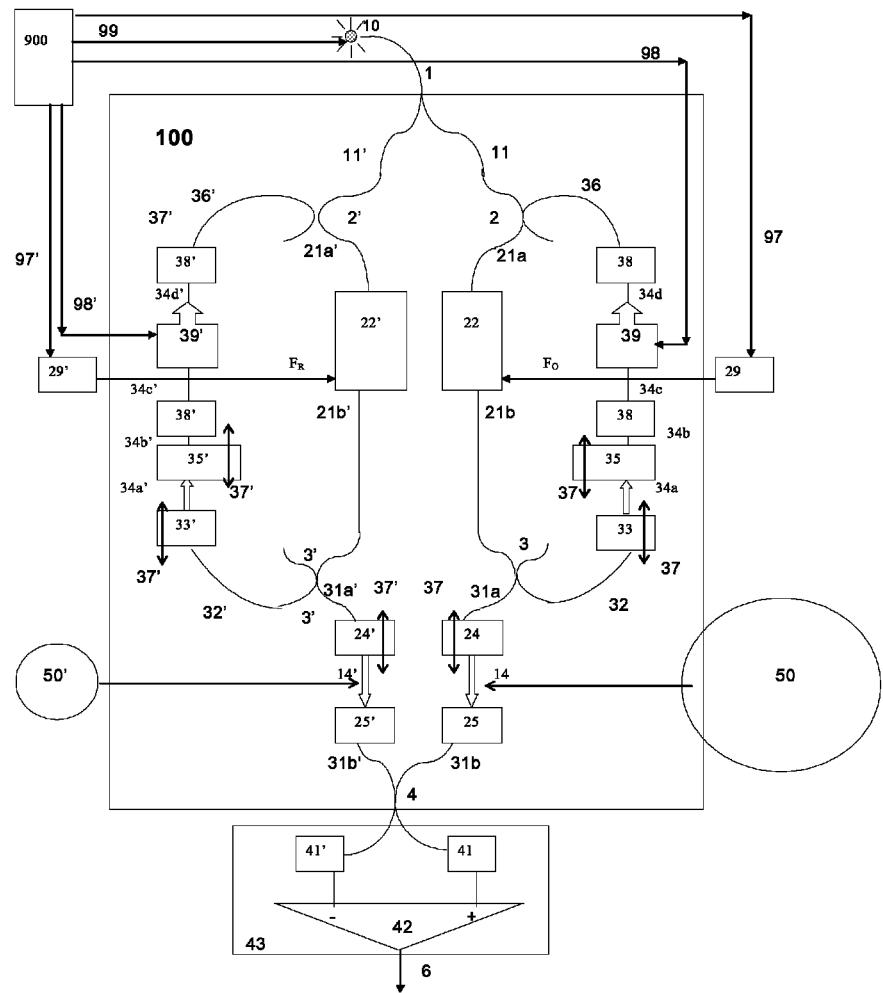
FIG. 3 shows another embodiment of the present invention, where losses are compensated by optical amplification.

In order to further compensate for losses in the embodiments in FIGS. 1 and 2, these can be equipped with optical amplifiers, 39 and 39', as shown in the improved embodiment in FIG. 3. Optical amplifiers could be solid state, such as commercially available semiconductor amplifiers (SOA) or fibre amplifiers, where different active media are now commercially available, together with their pump sources, such as Ytterbium doped fibre amplifiers. Any other type of optical amplifiers can be used.

In order to prevent reflections back into the optical amplifiers 39 and 39', optical isolators, 38 and 38' are used. The paths 34 and 34' have components 34a, and 34a' in air of lengths $a_{34}$ and $a_{34'}$ and components 34b, 34c, 34d, 34b', 34c', 34d' in fibre, of optical length $l_{34b}$, $l_{34c}$, $l_{34d}$ and $l_{34b'}$, $l_{34c'}$, $l_{34d'}$ respectively. The extra length due to amplifier 39 and isolators 38 is $l_{39}+2l_{38}$ in the recirculating object path and respectively $l_{39'}+2l_{38'}$ in the recirculating reference path. Therefore, the length of the recirculating paths become:

$$L_O=l_{32}+l_{33}+a_{34}+l_{35}+l_{34b}+l_{34c}+l_{34d}+2l_{38}+l_{39}+d_{21}+d_{22} \tag{10}$$

and $$L_R=l_{32'}+l_{33'}+a_{34'}+l_{35'}+l_{34b'}+l_{34c'}+l_{34d'}+2l_{38'}+l_{39'}+d_{21'}+d_{22'} \tag{11}$$

It should be obvious for those skilled in the art that other paths could be in air or the air path between 33 and 35 could be placed anywhere along the recirculating loop part not belonging to the main loop.

It should also be obvious for those skilled in the art that all paths could be in fibre and fibre stretchers could be used to adjust the OPD in the main loop by adjusting the main object path and the main reference path as well as to adjust the OPD in the recirculating loops by stretching the fibre in the recirculating object and reference paths.

Optical amplifiers could also be placed in the recirculating loops in FIG. 2 in the same spirit as illustrated in FIG. 3, to compensate for losses in the splitters 2 (2') and between launchers 33 (33') and 35 (35'). To achieve gain plus losses zero in the recirculation loop, less active gain is required for the optical amplifiers to be added to the embodiment in FIG.

2 than for the gain required for amplifiers to be added to the embodiment in FIG. 1 because FIG. 2 uses one splitter only to create a recirculating loop.

All sensing applications described in paragraph 6.1. in connection to the embodiment in FIG. 1 are equally applicable to the embodiments in FIGS. 2 and 3.

A particular application of the invention is that of a circular whispering-gallery (WG) resonator. Such resonators could be in the form of a microsphere made of a low-loss material. This manifests a high degree of confinement of light in WG modes which results in a high resonance quality factor (Q). Such resonators are used to detect tiny traces of optically absorbing chemical species by measuring Q. Even higher sensitivity is achievable by using the multiple path interferometer according to the invention.

Three possibilities exist:

(i) the recirculating loops in FIG. 2 are replaced with circular paths within resonators which exhibit WG modes, which allows a large number of recirculations without a supplementary amplifier. The splitter 1 drives two such whispering galleries resonators. A WG resonator is produced by tapping the optical fiber 11(21) and 11'(21') and approaching them to a circular structure, such as a silica sphere, where an induced wave can circulate a large number of times with little attenuation. The behavior of a resonator excited by a fibre is explained in "Wavelength-independent coupler from fiber to an on-chip cavity, demonstrated over an 850 nm span, published by T. Carmon et al in Optics Express, 15(12), (2997), 7677-7681. A microsphere placed within one wavelength of the core of an optical fibre absorbs light when the frequency of light in the fibre matches a resonant mode of the sphere). The wave will encounter a round trip time, $\tau$, for each traversal of the loop. Output light from the two resonators are sent to splitter 4, as in FIG. 2. The miniaturization of the galleries may prevent the utilization of modulators 22 and 22' and of the amplifiers 39 and 39'. A drop of an analyte placed close or on the resonant structure of the WG resonator induces a delay which is differentially amplified by comparing it with the multiple delay in the reference WG resonator in the other arm.

(ii) the fiber in the recirculating path is tapered and placed close to a WG resonator, where any of the embodiments in FIG. 1-3 can be used. For chemical analysis, an optical resonator is operated in the presence of a chemical compound. Usually, the concentration of the species is determined from its effect on the Q of the resonator. Here, the multiple round trips enhance the resonances, derived from broadband excitation. With two such resonators in the recirculating loops, very sensitive sensing is achieved by interfering the light resulting from the two recirculating loops. Interference will be achieved when the frequency of the two waves is identical only. Alternatively, using a swept very narrow optical source, comparison of resonances in the two resonators is achieved.

(iii) Alternatively, such a WG resonator can be placed instead of sensor 50 in the main sensing path. Such resonators use silica spheres, round trip delays are in the order of 0.1 mm. Scanning the $OPD_{main}$, multiple peaks are obtained for the coherence gate due to the multiple round trip in the resonator.

FIG. 4 describes a further embodiment of the present invention where scanning means are provided. In order to use the interferometers in FIGS. 1-3 for optical coherence imaging of an object, 50, signal is taken from the object part of the object path, either from path 11 or path 31, using a 5$^{th}$ splitter, implemented in FIG. 4 using a circulator, 5. Light is sent via object path 51 of length $s_{51}$ towards fibre launcher 52, of length $s_{52}$ towards a focusing element 53, which can be adjusted for focus via a translation stage 57, transverse scanner or scanners 54, 55 and interface optics 56 towards the object 50, encountering from launcher 52 up to the top of the object 50 a total air length $a_{50}$ and a glass length $s_{50}$. Then, the object path traverses the object round trip up to the depth of interest (which includes the index of refraction of the object) $z_{50}$. Light returned from the object 50 is launched into the circulator and then outputs along the path 31b.

For dispersion compensation, a similar path is incorporated in the reference path, using a circulator, 5', fibre length 51' and launcher 52', sending light towards a mirror, 58, via a reference path length $s_{51'}$, towards a fibre launcher 52' of length $s_{52'}$ respectively, and receiving light back which is being sent via optical reference path length 31b' towards the second input of the main splitter 4. A similar length of glass of lenses is incorporated, lens and group of lenses 53', 56' to compensate for the glass length in the lens 53, and other elements in the interface optics 56, along the optical path length, $s_{50'}$. In total, the reference path encounters a one way air length $a_{50'}$ and glass length $s_{50'}$.

Matching the OPD in the main loop requires:

$$s_{11}+d_{21}+d_{22}+s_{31}+2(s_{51}+s_{52}+a_{50}+s_{50}+z_{50})=s_{11'}+d_{21'}+d_{22'}+s_{31'}+2(s_{51'}+s_{52'}+a_{50'}+s_{50'}+z_{50'}) \quad (12)$$

To keep the dispersion low, preferably, the fibre and glass paths in the two main optical paths, object and reference should be substantially the same:

$$s_{11}+d_{21}+d_{22}+s_{31}+2(s_{51}+s_{52}+s_{50}+z_{50})=s_{11'}+d_{21'}+d_{22'}+s_{31'}+2(s_{51'}+s_{52'}+s_{50'}+z_{50'}) \quad (13)$$

and the path airs should be substantially the same $$a_{50}=a_{50'} \quad (14)$$

The path through the object should be compensated through an equivalent path through a similar material 50':

$$z_{50}=z_{50'} \quad (14')$$

This could be achieved by using a cuvette 50' of suitable thickness and corresponding refractive index inserted in the reference path between 5' and 58, of optical path length, $z_{50'}$. Alternatively, a spectral scanning delay line can be used in the main reference path, based on a diffraction grating and tilted mirror as disclosed in the patent application US 2006/0055936A1, to replace one of the optical modulator 22, 22' or both. In addition to the adjustment of the OPD, dispersion compensation can also be achieved using a spectral scanning delay line.

Preferably, the coherence position is adjusted first in the main loop actuating on the axial position of the object 50 and mirror 58 and then the recirculating loop OPD is adjusted actuating on 37 and 37' to alter $a_{34}$ and $a_{34'}$. According to the invention, such adjustment is independent to the adjustment of $OPD_{rec}$.

For dispersion compensation in the recirculating loops, of optical path difference $OPD_{rec}$, again a spectral scanning delay line could be used in one or both recirculating paths. In addition to dispersion compensation, such a spectral delay line provides frequency shifting. By shifting the incidence of the beam on the galvoscanner in the spectral scanning delay, a shift in frequency is added. This effect can conveniently be used to replace the Bragg cells or any expensive frequency shifters. Therefore, one such device in one of the arms or two such spectral scanning delay lines can be used, one in the recirculating reference path and another one in the recirculating object path. By synchronous control, when actuated in phase they can be used to decrease the interference frequency shift, ΔF or when actuated in anti-phase, they can be used to increase the interference frequency shift, ΔF. A It should be obvious for those skilled in the art that circulators 5 and 5' could be replaced by splitters with suitable coupling ratio. Alternatively, only one circulator in the object arm in FIG. 4 could be employed. Such a circulator could also be replaced by a single mode coupler or a bulk splitter. The reference path can be left as it is shown in FIG. 3. In this case, for dispersion compensation the cuvette or material 50' is inserted into the air path $a_{14'}$ and needs to have double the length of the object, $2z_{50}$.

It should also be obvious that the elements 51 to and including the object 50 could be inserted before splitter 2, by interleaving all these elements in the line 11 and inserting the splitter 5 there. Similarly, the elements 51' to and including the mirror 58 could be inserted before splitter 2', by breaking the line 11' and inserting the splitter 5'. Alternatively, both lines 11 (11') and 31 (31') are used for this goal, where main path adjustment means are introduced in one path, 11 (11') and dispersion compensation in the other path, 31 (31'). It should also be obvious that the interferometer could operate in a simpler form, if line 31' is not broken at all, remains wholly in fibre and no elements 5' up to 56' are needed, in which case some dispersion is tolerated.

For amplification of the object signal returned from the object 50, a supplementary amplifier can be added before the main splitter 4, as shown in dashed line by 39. To perform satisfactorily, the amplifiers require optical isolators 38. In some applications, one is sufficient, two are shown in FIG. 4 around each amplifier 39.

7. Multiplexed Sensing

Sensing applications are referred here as those which use a sensor like that in the inset in FIGS. 1 and 2, where the sensor could have multiple paths in transmission, to be incorporated in the sensing path in FIGS. 1, 2 and 3 or in reflection via a splitter or a circulator 5, in FIG. 4. In this case, the transversal scanner 54, 55 is not needed. The discussion here can however be extended to multiple interrogation of sensors using the scanners 54, 55, where the object beam is sent to multiple path sensors with their entries placed in the transversal section of the en-face plane perpendicular to the optic axis extending from 52 towards the object 50, replaced by a multipath sensor. Otherwise, sensing should also be understood as evaluating optical properties of the object 50 along its depth directions and starting from different transversal positions. An A-scan OCT which is a 1D scan is here understood as meaning an image as well as a collection of values in depth of the property to be sensed or measured.

There are several possible procedures to employ the interferometer 100 in FIGS. 1 to 4 for instantaneous demultiplexing of several sensors, based on TD-OCT or SD-OCT as disclosed immediately below.

7.1. Multiplexed Sensing Using Time Domain Low Coherence Interferometry

The optical source 10 is a low coherent source, let us say with a bandwidth and central wavelength determining a coherence length $l_c$. In this case, if the sensing paths are placed in transmission along the path 14 in FIGS. 1, 2 and 3, then the incremental delay d has to be larger or equal to the coherence length. If the sensing paths are in reflection, then d/2 should satisfy the condition of being equal or larger than the coherence length.

Let us consider a sensor with multiple paths in transmission and $l_c$=10 microns. Let us also consider the case where under the factors to be sensed, the variation of each path $z_m$ could attain values no larger than $\delta z$=1 mm. In this case, the sensing paths are devised to exhibit an incremental delay d=1 mm. Then, the $1^{st}$ sensing path varies from 4 mm to 3 mm, the $2^{nd}$ sensing path from 3 mm to 2 mm, etc, with the last sensing path, the $4^{th}$ in the insets in FIG. 1 and FIG. 2 varying from 1 mm to zero. Each carrier mΔF defines a channel. Cross-talk between the sensing channels is guaranteed as long as no sensing path varies by more than d=1 mm.

In this case, different OPD values of the sensing paths as determined by $z_m$ can be interrogated and simultaneous demultiplexing can be achieved using the invention by scanning the length of the $OPD_{main}$ for a swing of d. This can be achieved by installing one of the stages 25 or 25' in the main OPD on a motorized controlled stage. Alternatively, a spectral scanning delay line can scan $OPD_{main}$ over an axial range of d=1 mm by tilting its galvo-mirror. During the axial scanning of the $OPD_{main}$, if no drops are placed on the sensing paths, or no sensing action is applied to the sensor, then all channels will exhibit a maximum of interference for their carriers of frequency mΔF simultaneously. If the sensing action to be detected extends or shortens the OPD of each sensing path, then the time during the axial scanning when maxima occur in each channel differ. In this way, the exact timing when a peak is noticed in each channel relative to the start of scanning is a measure of the OPD in that sensing channel differing from the original path length value. Using a spectral scanning delay line operating at T=10 ms, with a coherence length of 10 microns and $\delta z$=1 mm, P=$\delta z/l_c$=100 points in axial distance are resolved where the time per each peak is T/P=0.1 ms which determines en electrical bandwidth of at least 20 kHz. For demodulation, this requires that the interference frequency ΔF is at least 40 kHz. The 4 channels required to interrogate the sensor with 4 sensing paths in FIGS. 1-3 will deliver pulses at different time moments within T corresponding to the respective length $z_m$ of the sensing path m=1 to 4.

7.2. Sensing Using Spectral Domain Low Coherence Interferometry

Channeled Spectrum OCT

Figure 5A:
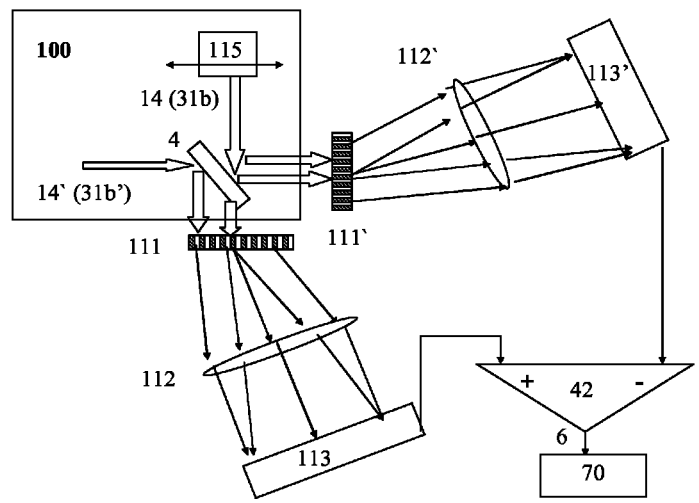
FIG. 5a illustrates an embodiment where the interference signal is spectrally analysed.

The interferometer 100 is used to illuminate one or two spectrometers instead of sending light towards the photodetectors 41 (41'), as shown in the embodiment in FIG. 5a. Light from the multiple interferometer 100, equipped with frequency shifters 22 and 22', comes along beams 14 and 14' in FIG. 1-3 and along beams 31b and 31b' in FIGS. 4 and 11, and are input to the splitter 4. The outputs of splitter 4 send light to one or two diffraction gratings, 111(111'), each grating followed by a lens, 112(112') and a linear photodetector sensor array, 113(113'), a CCD or a CMOS camera, to display the channeled spectrum. Then the outputs of the line cameras 113 and 113' are subtracted in the differential amplifier 42 and the result supplied to block 70, which in this case performs FFT. Usually, good signal to noise ratio can be obtained with only one spectrometer and the differential amplifier is not used, this is because usually, Fourier domain set-ups using spectral decomposition operate in shot noise regime. However, the balance of two spectrometers helps in reducing the autocorrelation terms. By using lateral displacing means 115, beams 14 (31b) and 14' (31b') are shifted laterally before being incident on the diffraction grating and they may not superpose at all, in which case mirror terms are eliminated based on Talbot bands as described in the patent application WO2005040718 (A1) (GB2407155 (A) or EP1687586 (A0). If mirror terms are eliminated based on complex Fourier transformation in each channel m, by using the carrier mΔF, then the lateral displacing means 115 it is not needed to eliminate the mirror terms. However, in this case, the lateral displacing means of beams 14 (31b) and 14' (31b') can be advantageously used as described in the application GB 0802290.7, 8, Feb. 2008, by A. Gh. Podoleanu, to shift the reference beam away from the object beam, where the zero order diffracted object beam can feed a simultaneous confocal channel. It should be obvious that a prism (or prisms) can be used instead of the diffraction gratings 113(113'), in which case the signal for the confocal channel is produced by reflection on one facet of the prism.

The signal read off the array after FFT leads to an A-scan according to principles known in the art of channeled spectrum OCT (or Fourier domain OCT). Therefore, in subsequent parts in the present disclosure, where a swept source 10 is used to implement a certain operation regime, channeled spectrum OCT can be equally applicable (based on the equivalence between the swept source and channeled spectrum OCT, as both methods are from the same category of spectral domain OCT methods) by replacing the photodetector 41 (and 41' depending the case) with a spectrometer (or spectrometers). In this case the signal read out of the photodetector sensing array(s) is modulated at frequencies m$\Delta$F. Modern CCD linear array cameras are known which can work over 100 kHz, this limits the modulation frequency to 50 kHz, i.e. to m=5 carriers at multiples of an interference frequency $\Delta$F=10 kHz. Further increase in the speed of reading of photodetector CCD and CMOS cameras and arrays will make such applications feasible, with a larger number m of round trips in the recirculating loops.

Figure 5B:
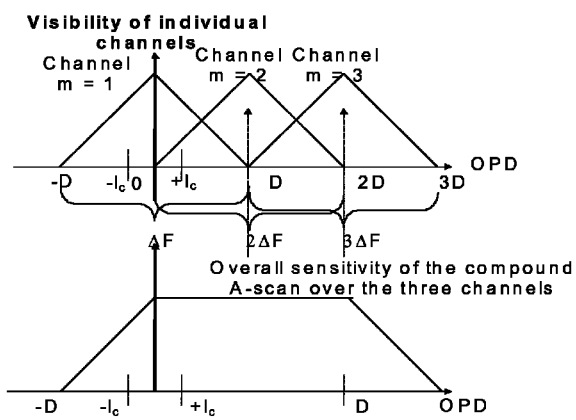

The optical modulators 22 and 22', preferably frequency shifters, allow as described before, elimination of mirror terms in the complex FFT signal of the signal(s) provided by the line camera(s). The principle, described in "Heterodyne Fourier domain optical coherence tomography for full range probing with high axial resolution", published by A. H. Bachmann, R. A. Leitgeb, T, Lasser in Optics Express (2006), 14(4), 1487-1496 leads to full range imaging, where the mirror term is eliminated and the range of OPD becomes −D to D, where D is the system axial OPD range, proportional to the number of grating lines illuminated multiplied by the grating periodicity. Each channel is coded on a multiple of the modulation frequency, m$\Delta$F. providing a full range OPD in each channel. Improvement in the sensitivity decay of FD-OCT method is obtained for low values m. This is shown in FIG. 5b. Doubling (m=2) or tripling (m=3) the range of a standard FD-OCT may be sufficient to provide a long A-scan or high quality images of the anterior chamber. Using a camera with 1000 pixels a FD-OCT system can reach a range D of approximately 2 mm and a full range of 2D=4 mm. In this case, with OPD$_{rec}$=2D, for m=2, 8 mm or with m=3, a 12 mm full range is obtained, this will allow seeing the cornea and the eye lens in a single B-scan OCT image. Each scan in the array provides for m=3 three A-scans, over 3 tracks. Better sensitivity profile can be obtained by superposing the positive range of the OPD of the mth channel with the negative OPD range of the m+1 channel. This is shown in FIG. 5b for OPD$_{rec}$=D and m=1, 2 and 3. Top shows the visibility of each channel. Around each carrier, in each channel, a full range A-scan is obtained using the modulation on the carrier m$\Delta$F. When summing up all channels, the sensitivity in the bottom part of the FIG. 5b results, constant between 0 and 2D=4 mm and a total range from −D to 3D-4D=8 mm. This is a unique feature of the present invention. Obviously, by playing with the relative value of the OPD$_{rec}$ and the range given by the spectrometer resolution, D, the total axial range can be expanded to 12 mm with some variation in the sensitivity.

In opposition to the swept source case described below, the modulation frequency required is much lower, so $\Delta$F is produced by the difference of the frequencies F$_O$ and F$_R$. In this case, a spectral scanning delay line may suffice as 22 or 22', instead of Bragg cells.

7.3. Swept Source Interrogation

The optical source 10 is a coherent source, of linewidth $\delta\lambda$ which is tuned within a bandwidth $\Delta\lambda$. To achieve similar axial resolution as given by the examples above using a low coherence source, the tuning range $\Delta\lambda$ should be similar to the bandwidth of the low coherence source employed in the previous example. Using principles of swept source low coherence interferometry, the multiple OPD values due to the recirculating paths and due to the sensor are simultaneously scanned along an axial distance determined by the source line-width, $\delta\lambda$. Because the multiple path sensor has OPD values in steps of d, then the line-width $\delta\lambda$ should be sufficiently small to determine a swept source interferometry depth range of at least d/2. With $\Delta\lambda$ in the range of tens of nm, for a central wavelength of microns or submicrons, $\delta\lambda$ should be a few nm. By sweeping the optical frequency of the source, multiple signals of carrier frequencies m$\Delta$F are generated, all present in the photodetected signal 6. If these are mixed with sinusoidal signals of m$\Delta$F in each channel m, then each resulting channel signal represents a swept source interference signal. FFT of the resulting signals according to means known in the art, leads to an A-scan in each channel. These A-scans extend in axial distance for as long as the coherence length of the sweeping source is, either side of the OPD=0 value. The OPD=0 in each channel is stepped by OPD$_{rec}$. Therefore, mirror terms will corrupt the compound image formed from the many A-scans. This can be eliminated by generating the complex FFT for each channel, using signal processing based on frequency shifting in each channel. The same procedure mentioned above for FD-OCT as described in "Heterodyne Fourier domain optical coherence tomography for full range probing with high axial resolution", published by A. H. Bachmann, R. A. Leitgeb, T, Lasser in Optics Express (2006), 14(4), 1487-1496 can be used for swept source OCT as well. Let us say that the axial range determined by the linewidth is D=1 mm and the OPD$_{rec}$ was adjusted to match D, as shown in FIG. 5b. In this way, if n channels are used, the main channel on $\Delta$F determines an A-scan which starts from −1 mm to 1 mm in the sensor track, the first recirculating interference signal determines an A-scan which starts from a depth in the sensor of 0 and extends up to 2D=2 mm, and so on. The information from the main channel (the 1$^{st}$) for the range 0-D is on the right of the OPD=0 in the 1$^{st}$ channel, but on the left of the OPD=0 in the 2$^{nd}$ channel (the 1$^{st}$ recirculating channel). These two signals will superpose each other and advantageously contribute towards reduction of sensitivity with OPD (the sensitivity in the 1$^{st}$ channel decreases from OPD=0 to the right while the sensitivity in the 2$^{nd}$ channel increases from OPD=−1 mm in the 2$^{nd}$ channel (coinciding with the OPD=0 in the 1$^{st}$ channel) towards OPD=0 in the 2$^{nd}$ channel (coinciding with the OPD=1 mm in the 1$^{st}$ channel). In this way, the invention addresses one of the main disadvantages of spectral interferometry and SD-OCT, decay of sensitivity with depth. The axial positions of peaks in the A-scans determine the value of OPD in the individual sensing channel within the sensor which depends on the quantity measured. Because the bandwidth of the photodetected signal when sweeping the laser frequency at 10 kHz could reach 10 MHz for 1000 peaks in the channeled spectrum scanned, a large frequency carrier is necessary. Therefore, it is preferable for this application to operate on the sum of frequency shifts, $\Delta$F=F$_O$+F$_R$.

8. Automatic Dispersion Compensation With Depth Exploration

When OPD$_{rec}$=0, all the OPD values of the multiple recirculating paths in FIG. 1-4 are equal and the interfering object and reference waves are matched for the same axial position in the object as seen by the $OPD_{main}$. Let us consider that the $OPD_{rec}=L_O-L_R$ is initially adjusted to zero by matching the fibre lengths in the two recirculating object and reference arms as well as matching the air lengths. Then, by introducing an adjustable thickness water filled cuvette or a cuvette or a slab with a liquid of index of refraction close to that of the object investigated, depth advancement from one depth to the next (from one number m of recirculations to the next, m+1) is performed automatically with perfect dispersion compensation. This is shown by the cuvette 65', of optical path length, δ, introduced in the air recirculating path, 34a' in FIG. 4. Obviously, the slab or cuvette 65' could be introduced anywhere in the recirculating reference path which is not shared with the main reference path. With $OPD_{main}$ adjusted to the top of the range in depth to be scanned in the object 50, each round trip through the recirculating loops adds the $OPD_{rec}=\delta$ and in this way, an automatic dispersion compensation is achieved for signals collected from different depths, z, in the object, 50, to be investigated, with $L_R=L_O+\delta$. Alternatively, the main OPD is adjusted up to a reference depth inside the object given by the thickness of the cuvette 50' and the slab of thickness $OPD_{rec}=\delta$ is placed in the object recirculating arm, 34a. In this case, i.e. $L_R+\delta.=L_O$, the A-scanning proceeds towards the surface, still ensuring dispersion compensation at each step equal to δ. This method is superior to all known methods of dispersion compensation, where the depth advancement is performed by changing an air path length.

This procedure is equally applicable when using a low coherent source 10 and involving principles of time-domain coherence gating as well as when the optical source 10 is a swept source. In this later case, the interferometer 100 can be used to speed up the acquisition of an A-scan from a given long depth range by acquiring multiple A-scans from subdivisions of the depth range, as disclosed further below.

9. Oct Regimes Of Operation Using A Low Coherent Source
9.1. C-Scan Imaging at Several Depth Simultaneously The transverse scanners 54 and 55 in FIG. 4 are driven by suitable electrical signals according to procedures known in the art of scanning and an en-face (constant depth or C-scan) OCT image is generated from a depth given by $OPD_{main}=0$. The two scanners are driven by lines 81 and 82, which control the frame and line scanning performed by the driver or drivers 85. For T and C-scans, both signals could be saw-tooth or triangle, if a polygon mirror is used, then 81 includes a synchro signal from the polygon driver towards the electronics controlling interface and PC 80.

The photodetected signal, 6, delivered by the photodetection unit 43 is sent to a demodulator 70. In the simplest form, this is a tunable band pass filter (BPF), which could be tuned on the carrier frequencies, multiple of $\Delta F=|F_O-F_R|$ or $\Delta F=F_O+F_R$. Preferably, the BPF should exhibit an electrical bandwidth to accommodate the image bandwidth or the bandwidth required by the sensing application. RF analysers are known which can provide output from their scanning head, within selectable bands centered on selectable frequency values. Several HP RF analyzers (now Agilent) allow adjustment of the central frequency in the band 0.1 to 2900 MHz with a bandwidth adjustable from 1 kHz to 1 MHz, have the possibility to stop the span and be transformed into a genuine band pass filter with adjustable band pass and low pass filtering and outputs the video signal in log or linear form.

An embodiment of the demodulator 70 according to the invention is shown in FIG. 6a. Band pass filters 75 are followed by rectifiers 66 producing amplitude signals $A_1$, $A_2$, ... $A_n$. These are fed into a multiple channel frame grabber 64 which produces all n C-scans simultaneously and places them into a 3D imaging volume, a voxel. The voxel is then sent via 71 to the electronics interface block and PC 80. In this way, all n C-scan images are obtained in the time of generating one en-face OCT image.

Alternatively, 70 could be an A/D board followed by an FFT processor to provide band pass filtering, taking the role of all BPF 75 on all carriers, taking the role of all 66 rectifiers and delivers compound signal 71 consisting in amplitude of brightness within the C-scans stack. Such processing can additionally provide the phase of each signal, on each channel. An amplitude voxel as shown in the inset in FIG. 6a is produced by a multiple channel frame grabber 64. This can equivalently generate an additional phase 3D voxel. The electronics controlling interface and PC 80 contains a frame grabber to display all the voxel or in a simpler format, a single image as selected by 70 if 70 is equipped with a single tunable band pass filter 75. Alternatively, demodulator 70 demodulates several or all channels simultaneously and the PC 80 contains multiple frame grabbers and multiple displays to present the user several images simultaneously.

If $OPD_{rec}$ is different from zero, then each pair of recirculating waves, one object and the other the reference, for each roundtrip in the two recirculating object and reference loops will interfere constructively from depths $OPD_{rec}$, $2OPD_{rec}$, $3OPD_{rec}$, ... $mOPD_{rec}$, ... etc in the object, starting from the depth or axial distance as selected by the $OPD_{main}$. Let us say that the coherence length of the source is $l_c=10$ microns, which determines a depth resolution of 5 microns. Let us adjust the differential delay $OPD_{rec}$ on 20 microns, larger than the coherence length to secure sufficient separation between the channels. In this case, if the multiple path interferometer according to the invention targets M=100 depths simultaneously, this will cover 1 mm from tissue with a sampling rate of 10 microns (half of the value $OPD_{rec}$ due to the roundtrip to the object and back).

The photodetected signal contains frequencies $(m+1)|F_O-F_R|$. By demodulating the amplitude of the RF on each multiple frequency of ΔF, the reflectivity of the layer at each depth $z_m$ is obtained and C-scan OCT images at depths $z_m$, C-scan$_m$ are generated (using the signal in the main loop for m=0 and using the signals in the recirculating loops for m equal and greater than 1).

9.2. B-Scan Imaging

Let us say that M=20 channels, j=1,2, ... 20 operate simultaneously, on carriers ΔF, 2ΔF, ... mΔF, up to 20ΔF. A B-scan image of M T-scan lines can be produced in the time required for only one T-scan, i.e. the embodiment in FIG. 4 speeds up the acquisition of a M lines B-scan by a factor of M in comparison to the case where the main loop is used only. The differential delay between channels, $OPD_{rec}$, is preferentially adjusted equal or less than the coherence length, $l_c$. The M T-lines correspond to M transversal profiles of reflectivity from depth positions $Z_i+mOPD_{rec}/2$ with m=0, 1, 2, ... to M=20. The B-scan has the lateral size imprinted by the transverse scanner, 54 (or 55) and the depth range is $R=(M-1)OPD_{rec}/2$. For a value $l_c=10$ microns, let us say that $OPD_{rec}=l_c$, in which case R=95 microns.

This is the case illustrated in FIG. 6b, where a B-scan OCT images is created in the time to acquire a T-scan, where several T-scans are generated simultaneously, as the number of channels in the interferometer 100. The T-scans are placed on a display in 80, which simultaneously receive signals for separate T-scans, placing them on different raster lines at the same time.

If a longer depth range is required, then a repetition of acquisition of M lines at new depth positions $Z_i$, controlled along the line 84, distant apart by R, can lead to a deeper range B-scan OCT image. Let us say that P=5 such B-scans of M lines are acquired, then the final B-scan has a depth range of $(PM-1)OPD_{rec}/2=99OPD_{rec}/2$. For the example above, the synthesized B-scan image has a depth range of 495 microns, from i=1, 2, ... up to P=5 stripes each of 20 lines.

The procedure is also compatible with dynamic focus, where synchro pulses are sent via the line 84 in FIG. 4 to advance the OPD as well as to the stage controlling the focus adjustment means, 57, via line 83. For a number of P times, the focus position is changed by the electronics controlling interface 80 via line 83 which actuates on the focusing element 53 in the object interface optics between the launcher 52 and the object 50. If the T-scanning operates at 0.5 kHz, with a repetition time $T_{line}$=1 ms per each T-scan a round trip scan, left-right and then right-left, then M lines take $MT_{line}$ time, i.e. 10 ms for a M=20 lines B-scan stripe image from a depth R=95 microns. If P repetitions are proceeded, then the time required is $MPT_{line}$ which with the values of the example above, lead to 50 ms to assemble a 495 microns B-scan frame, i.e. a frame rate of 20 Hz becomes possible. This is comparable with the acquisition speed of spectral domain OCT, with the advantage that better sensitivity is achieved due to the implementation of the dynamic focus, not possible in spectral domain OCT.

Furthermore, using a resonant scanner at 16 kHz the fastest speed in B-scan image generation can be achieved corresponding to a frame acquisition equal to the line rate, i.e. 16 kHz. This could lead to extreme frame rates of 16×20=320 Hz.

9.3. Generation of a Larger Depth Range Image for Guidance of the OCT Investigation If the object is the retina, then it will be useful to generate an image with the aspect of a scanning laser ophthalmoscope (SLO) system. To obtain such an image, en-face (C-scan) images from a depth range comparable to that of an SLO are required. For instance, a depth of at least 300 microns should be covered. This could be achieved for example with 10 images at $OPD_{rec}$=30 microns axial depth difference. Then, all 10 C-scan images are summed pixel by pixel to synthesize an SLO image corresponding to a depth range of 300 microns. Two Possibilities Exist:

(i) 10 channels are demodulated on $|F_O-F_R|=\Delta F, 2\Delta F, \ldots 10\Delta F$, RF signals are rectified independently and then are summed up. For instance, if $\Delta F$=1 MHz, 10 RF tuned BPF filters on 1, 2, 3, ... 10 MHz are used followed by rectifiers. Each filter has a bandwidth to the extent of the image bandwidth. In general, a compound image of amplitude $A_{integral}$ is constructed using a weighted sum over m channels using the amplitudes $A_i$:

$$A_{integral}=\Sigma_{i=1}^{m} w_i A_i \quad (15)$$

where $w_i$ are weighting coefficients.

(ii) The photodetected signal is processed not on independent RF frequencies separately, but using a large band amplifier to cover all channels within the photodetected spectrum. For example, if $|F_O-F_R|$=1 MHz, a band pass filter of 10 MHz should suffice to acquire the information from all depths and then followed by a single rectifier. In this case, it may be advantageous to reduce the modulation frequency $|F_O-F_R|$ below the value of the image bandwidth, in order to reduce the electronic bandwidth and the noise.

9.4. Tracking

One of the immediate advantage of the invention is its ability to track fast movements of a mirror. In FIG. 4 let us say that the object is the cornea of an eye whose axial position is to be tracked. The transversal scanners 54, 55 are not needed. The position of the cornea can be tracked with a resolution determined by the $OPD_{rec}$. Let us say that initially the cornea was adjusted to be at $OPD_{main}$=0. The axial position is determined by the channel m in FIG. 6a which outputs signal of frequency $m\Delta F$ suggesting that the axial distance is $(m-1)OPD_{rec}$.

10. Polarisation Sensitive Imaging

Each round trip of light through the recirculating loops can be used to alter or rotate the polarization of the light and send a different orientation of the linear polarization towards the object 50. Let us consider that the recirculating $OPD_{rec}$ is brought to zero. In this case all multiple waves reaching the 4$^{th}$ splitter 4 will be from the same depth, $z_{50}$ in the object 50. However, their polarization may be different. For instance, let us say that a linear polarized state, along the vertical direction, is launched into the splitter 1, using a linear polarizer, 61, and half-waveplates, 62 and 62' in the recirculating paths are oriented at 45° degrees in respect to the direction of the incident polarization in path 36 and 36' respectively. This results in a rotation of the linear polarization by 90 degrees being sent to the main loop along path 21a after the first round trip, with a horizontal orientation. Then at the second pass the polarization is rotated back to the initial direction. This leads to injection of orthogonal linear polarizations in the object, 50, which correspond to odd and even frequencies of the carriers in the photodetected signal.

If a quarter wave plate, 63, is used in the object path between the splitter 5 and the object 50, at 45 degrees from the linear polarization coming from splitter 5, then the succession of orthogonal linear polarization states above leads to injection of alternate circular polarizations into the object, with different helicities, toggled at each round trip through the two recirculating loops. The photodetected signals on odd and even frequencies $\Delta F$ correspond now to orthogonal circular polarizations. Another quarter wave, 63' is introduced in the reference path. Alternatively, the polarization in the reference path is maintained at 45° from that of the two orthogonal linear directions in the object path, by removing 62' and placing a half-wave plate 62" oriented at 22.5° from the direction of linear polarization of the reference beam, before the 4$^{th}$ splitter. This will project linear polarizations along the horizontal and vertical directions and lead to interference irrespective of the orientation of the polarization in 31a.

Similarly, a large variety of polarization states could be injected by using waveplates at different angles than 45 or 90 degrees. Signals at different frequencies within the photodetected signal 6 will represent different polarization states of the object. Alternatively, the optical modulators are phase or polarization modulators and not frequency shifters, as preferred above, in which case at every circulation, the polarization is rotated. 22 and 22' could equally include both a frequency shifter and a phase modulator driven by a DC voltage to secure a certain step in phase or polarization.

The polarization components are shown in dashed line as they are not required for all functions of the embodiment in FIG. 4.

11. Phase Shifting Interferometry and Despeckle

Procedures inspired from phase shifting interferometry could also be applied, if the differential recirculating path $OPD_{rec}$ is adjusted to a fraction of wavelength. This procedure can be applied to any frequencies in sequence in the photodetected signal. A minimum of 3 such frequencies can be used in which case the differential recirculating OPD is adjusted on a value equal to the central wavelength/3. Hilbert procedures can also be used, by employing two phase shifts only, in which case every pair of two adjacent frequencies could be used.

With reference to FIG. 7, let us say that K shifts are required, where the main and K−1 other recirculating loop channels provide signals $S_1, S_2, \ldots S_K$. For instance, if K=5, then $OPD_{rec}$ is adjusted to ⅕$^{th}$ of the central wavelength. In this case, 5 bands of image bandwidth centered around the first 5 RF frequencies, $(m+1)|F_O-F_R|$ with m=0,1, ... 4 are selected from the photodetected spectrum of signal 6. The signals $S_1, S_2, \ldots S_K$ are interferometer signals which are shifted in frequency to the base frequency by removing their carrier frequency. This is achieved using the embodiment of the demodulator 70 shown in FIG. 7. First, band pass filters 75 select RF signals around each carrier, $m\Delta F$, providing m channel signals, where they represent interference signals pulsating at the carrier frequencies $m\Delta F$. Then they are mixed with signals pulsating at $m\Delta F$, produced by multipliers 78, in mixer blocks 76, consisting of a mixer followed by a low pass filter. A mixer 72 is used to generate the difference in frequency of the two driving signals of the two frequency shifters, 29 and 29', to obtain the interference frequency shift, $\Delta F$. Alternatively, if only one frequency shifter is used in the multiple path interferometer 100, then block 72 is not needed and the signal 77 is the signal pulsating at the interference frequency shift $\Delta F=F_O$ or $F_R$ which is applied to mixers, 76, to produce signals pulsating at multiple of $\Delta F$, $m\Delta F$. The output of mixers 76, signals $S_m$, pulsate in the base band and carry the phase information of the interference corresponding to delays $mOPDrec$.

Differences are constructed which are then squared. Square root of the sum of squared differences will lead to the strength of the interference signal, similar to procedures utilized in phase shifting interferometry for each pixel in the C-scan image. According to phase shifting interferometry, the amplitude of interference can be approximated by:

$$s = \sqrt{0.5 \sum_{i=1}^{K} \sum_{j}^{K} (S_i - S_j)^2} \quad (16)$$

This numerical evaluation is performed in the Mathematics processor 79. In case 3 phase shifts are used only, the main and the next two recirculating waves are used only. In this way, a C-scan is produced without rectification for every K=3 consecutive channels. Obviously, the procedure can be extended to K=5 steps obtained from 5 channels, or any other number of steps. For K=3, the $1^{st}$, $2^{nd}$ and $3^{rd}$ channels are used to produce a C-scan image for p=0, the $2^{nd}$, the $3^{rd}$ and the $4^{th}$ channel produce a C-scan image for p=1 and so on. In this way, for every group of three consecutive interference images, a C-scan image is sent along the line 71 to the electronics interface and PC 80, giving C-scan images from depths differing by $\lambda/K$. They are similar, as collected from within a coherence length, however the phase inside each image is different and they could be summed over half of the coherence length, i.e. for signals obtained for a subdivision of p, $p'=Kl_c/(2\lambda)$. In this way, $p/p'$ distinct C-scan images are constructed, by averaging p' images to generate a different depth C-scan, from depths separated by $l_c/2$.

In addition to rectification and evaluation of scattering points in depth, the method can also be used to provide phase information by collecting as many phase values as required.

This procedure can also be used to eliminate speckle in the image by averaging over the phase diversity of the OCT signal.

12. Flow Imaging

Let us say that the object beam is incident on a vessel flown by a liquid inside the object 50. The frequency of the OCT signal is shifted by the flow with a Doppler shift, $D(z)$, where z is the depth in the vessel, with its edge at $z_0$. This combines with the modulation at $m\Delta F$ giving components of frequency $f_m = m\Delta F + D(z)$ or $m\Delta F - D(z)$. If axial movement takes place, then a Doppler shift, $f_{mov}$ is added as a frequency shift to the frequency registered in each channel. This does not depend on the depth within the vessel. By collecting simultaneously several Doppler shifted signals from different depths, z, in the object, a flow profile independent of axial movement is obtained in the following way, as provided by the embodiment in FIG. 8. First, the frequency shift is obtained in each channel by beating the signals provided by the band pass filters tuned on $m\Delta F$, 75, with sinusoidal signals pulsating at $m\Delta F$. Beating can be achieved using mixers followed by low pass filters in blocks 76. The output of mixers 76, signals $S_m$, pulsate at different frequency shifts in each channel, $F_m$. Then, a component or several in the set of signals are identified which originate in points outside the vessel, from depths less than $z_0$, providing a reference, $f_{mov}$, for instance the frequency of the signal from the first channel, $S_1$, or several, challes, $S_1$, $S_2$, and $S_3$. These carry a shift in frequency due to movement of the tissue only. The shift of the first carrier, due to the main loop, and the shifts of one or more of the next harmonics $m\Delta F$ due to the recirculating loops, if outside the vessel (up to $z_0$) provides $f_{mov}$. The next harmonics due to the cumulated delay in the recirculating loops correspond to advanced depth values into the tissue, so they are from inside the vessel. Then $f_{mov}$ is subtracted from all the other channel frequencies, $f_m = m\Delta F + D(z) + f_{mov}$, to produce the flow speed distribution within the vessel of the different channels frequencies in the block 73. This could again consist in mixers, one for each channel, mixing the output $S_m$ with the signal from the tissue outside the vessel, $S_1$ (or with the average of frequencies due to movement collected from several channels). In this way, the remaining shifts represent Doppler shifts due to flow only and the flow profile in the vessel is obtained unaffected by axial movement, in the mapping block 74, which produces a map of frequency values $F_m = f_m - f_{mov}$ versus depth $mOPD_{rec}$. If no movement takes place, then no shift occurs and the frequency of channels is $m\Delta F$. The frequency subtraction block 73 provides the frequencies $F_m$ which are movement free.

13. Storing Data 3D Imaging

Let us consider m=100 channels tuned on multiples of $\Delta F$, and $\Delta F=1$ MHz, which allows an image bandwidth of up to 0.5 MHz, compatible with acquisition of C-scans at a few Hz frame rate with images having a lateral size of a few hundred of pixels as discussed in 9.1. Let us say that a C-scan frame of N=100 lines is acquired at 1 ms line rate in T=0.1 s. In that case, if a stream of data is stored in the time for a frame, T, then this stream contains all the frames from the main loop channel and from the recirculating channels. Later on, after acquisition, a tunable RF band pass filter can be tuned on different frequencies to implement a specific channel which provides a C-scan at the incremental depth as determined by multiple of $OPD_{rec}$. This can be performed using the embodiment in FIG. 9. Signal from the photodetection unit 43 is digitally transformed by an A/D converter, 91 and its digital format is stored by storage means, 92. This could be in the form of a cyclical shift register which could be read cyclically with a period T. The batch of digital data is stored in synchronism with trigger signals provided by the driver, 85, of the transverse scanners along lines 81 and 82. The storage in the reading process provides the video signal along line 93 and the triggers for synchro 94. The video signal 93 is transformed in an analog version in the D/A converter 91', therefrom is sent to a tunable RF band pass filter, 96, equipped with a rectifier. The demodulated signal is then sent towards a frame grabber, 97, inside the interface electronics block 80, together with the synchro trigger 94 to synthesize an image. By tuning the RF band pass filter 96, while the storage 92 is cyclically read, a C-scan image is displayed at every time interval T and depending on the tuned frequency, it corresponds to a different C-scan slice in the volume acquired.

It should be obvious for those skilled in the art that other means are applicable, including whole digital processing where the signal is maintained in digital format and a FFT is evaluated on different tuned central frequencies.

Alternatively, the information provided by each channel is the phase, $\Phi_m$ in each channel. The phases $\Phi_m$ can be evaluated by numerical processing, implementing Hilbert or Fourier transformations and maps in the form of phase C-scan images are generated. Further, reference can be taken from the frequency shift signal, or frequency $\Delta F$. Even further, different functionality is achieved if reference is taken from signals pulsating in synchronism with signal of frequency $\Delta F$, but pulsating at multiples of $\Delta F$. Phase maps can be acquired at different depths simultaneously. Difference of phases in each pixel across different depths can be easily achieved to provide information on tiny changes, such as cytoplasm movements of cells or embryos.

Alternatively, the storage 92 can be used to store multiple T-scans, and in the process of reading the storage, the frame grabber 97 assembles all these T-scans into a B-scan image.

14. Angular Compounding for Speckle Reduction

A delay element 99, as shown in dashed line in FIG. 4 can be inserted into the collimated part of the object beam, to implement a method of angular compounding as described in "Speckle reduction in optical coherence tomography by "path length encoded" angular compounding", published by N. Iftimia, B. E. Bouma, and G. J. Tearney, in J. Biomedical optics, 8(2), 260-263 (2003). Then the beam is sent via the interface optics 56 towards the object. Two implementations of a two steps delay element 99 are shown in FIGS. 10*a* and 10*b*. Two slides, 102, of thickness larger than the depth range of the object are inserted half way into the beam in FIG. 10*a*, which shows a frontal view of the beam intersected by the plates sampling in transversal section areas marked 0, 1d, 2d corresponding to the amount of delay encountered by the beam traversing the device 99 made from the two slides 102, where d is the single pass delay introduced by the plate. A converging element in the interface optics 56, in the form of a lens 101, as shown in the lateral view of the embodiment in FIG. 10*b*, focuses the object beam on the target. The transverse scanner is not shown, it can follow after the delay element 99 or after the focusing element 101 with a subsequent use of other focusing elements.

Instead of slides halfway through the beam in FIG. 10*a*, the device in FIG. 10*b* is introduced fully into the object beam. For instance, for the embodiment in FIG. 10*a*, rays within the object beam encounter three delay values, 0, 1d, 2d. These rays approach the object at different angles, procedure which establishes a coding of angle on the OPD value encountered. The rays going through part marked 1d encounter an optical delay d, however after reflection on the object, they could return via the same part, encountering 2d, via the sector marked 2d, in which case the optical delay is 3d, or skipping the microscope slides, which gives an optical delay d. For pairs of rays traversing the delay element 99, one ray going towards the object and another ray returning, different possibilities exist. The table below shows the resulting delay values encountered by rays traversing the same or different sectors of the element 99.

TABLE 1

| Pair of sectors traversed | 0, 2 | 1, 1 | 0, 1 | 1, 0 | 1, 2 | 2, 1 |
|---|---|---|---|---|---|---|
| Minimum Delay (similar sector) | 0 | 2 | 0 | 0 | 2 | 2 |
| Medium delay (mixed rays) | 2, 2 | 2, 2 | 1, 1 | 1, 1 | 3, 3 | 3, 3 |
| Maximum Delay (similar sector) | 4 | 2 | 2 | 2 | 4 | 4 |

Out a total of 24 possibilities, there are 3 possibilities for the 0 delay, 3 possibilities for the 4d delay, 4 possibilities for the d delay, 4 possibilities for the 3d delay and 10 possibilities for the 2d delay. This means that with 2 steps, 5 delays for 5 possible incidence angles are coded into the object beam returned to the interferometer. This allows average of the speckle over 5 different angles. To implement the speckle average, the main $OPD_0$ value is tuned to the desired depth in the tissue, which uses the rays traversing the sectors in the optical delay element 99 encountering a 4d optical delay. Then the $OPD_{rec}$ is adjusted to match the delay d, which tunes the multiple path interferometer to the same $OPD_0$ minus a step d for each round trip of the waves through the recirculating loops. The $1^{st}$ recirculating loop uses the sectors in the element 99 which determine a delay 3d, the $2^{nd}$ recirculating loop uses the sectors in 99 which determine a delay 2d and so on. The amplitudes corresponding to the delays 0, d, 2d, 3d and 4d are $3/24$, $4/24$, $10/24$, $4/24$ and $3/24$ respectively. When summing the 5 C-scans, weighting coefficients are used inverse proportional to these coefficients. The five C-scans originate from the same depth in the object but are produced using five different incident angle incoming rays, in this way, angular compounding results and less speckle.

The circular symmetry of the embodiment in FIG. 10*b* ensures a better control of the corresponding angle of rays which encounter a specific delay. All rays from a sector encounter the same incidence angle.

The embodiments in FIG. 10 implement 2 delays only, however this was for illustration only and it should be obvious for the person skilled in the art that more delay steps or any, P, can be incorporated in the same way with 2P+1 channels being used to average over 2P+1 incident angle values.

15. B-Scan Imaging Using Spectral Domain Oct

The multipath interferometer 100 can be used to speed up the acquisition of an A-scan from a given long depth range by acquiring multiple A-scans from subdivisions of the depth range. Let us say that the depth range is relatively long, R=10 mm, which is a problem for current SD-OCT technology. This can be divided into 10 stripes of axial length d=1 mm each. The optical source 10 is a coherent source, of linewidth $\delta\lambda$ which is tunable within a bandwidth $\Delta\lambda$. Using principles of swept source low coherence interferometry, the multiple stripes are simultaneously scanned axially while the transversal scanner 54 or 55 (or both) scans (scan) the object beam transversally along a 1D profile. The line-width $\delta\lambda$ should be sufficiently small to ensure a depth range of the swept source OCT up to at least d=2d=2 mm (OPD round trip). This application is especially useful in applying the principle of swept source OCT for a long axial length when the line width is not sufficiently small to ensure scanning of the whole depth range. For instance, for a central wavelength of $\lambda$=1 micron, a line-width of 0.5 nm allows swept OCT scanning up to approx. d=1 mm depth, but for a B-scan of 10 mm, the linewidth needs to be smaller than 0.05 nm, technically difficult to achieve. By sweeping the wavelength of the optical source, multiple signal of carrier frequencies m$\Delta F$ are generated within the photodetected signal 6. These are mixed with sinusoidal signals of m$\Delta F$ in each channel m, as shown in FIG. 7. Signals $S_m$ in each channel m represent swept source interference signals. FFT of the resulting signal $S_m$ is performed in block 79 according to means known in the art which leads to an $m^{th}$-channel A-scan. These A-scans extend in axial distance for as long as the coherence length of the sweeping source is. In this way, if n=10 channels are used, the main channel on ΔF determines a B-scan which starts from a depth in the object 50 which sets the top or the bottom of the compounded 10 mm depth B-scan and extends up to d=1 mm from this reference depth, either deeper or towards the surface. The first recirculating interference signal determines a B-scan which starts from a depth in the object from the previous reference depth plus d or minus d and extends up to 2d more in depth or towards the surface by 2d, and so on up to the $9^{th}$ recirculating channel. The $n^{th}$ B-scan stripes are then assembled together in the interface 80 to obtain a synthesized B-scan image. This is obtained in the time to generate a B-scan image for the depth of a stripe.

Because the bandwidth of the photodetected signal when sweeping the laser frequency could reach tens of MHz, a large frequency carrier is necessary. Therefore, it is preferable for this application to operate on the sum of frequency shifts, $\Delta F = F_O + F_R$.

The same principle can be implemented using spectrometers instead of photodetector 41 (and 41') according to the comment above in the paragraph on sensing, 7.2., to implement channeled spectrum OCT. In this case, multiple A-scans are generated for different transversal points selected by the transverse scanner 56.

16. Pulsed Operation and Control of the Amplifies Spontaneous Emission (ASE)

The larger the bandwidth of the loops using optical amplifiers, the larger the ASE contribution. The embodiments using optical amplifiers are characterized by a continuous buildup of ASE at each roundtrip of light through the loops. Large bandwidth is essential for good depth resolution, therefore the larger the bandwidth, the larger the ASE. This can be controlled by switching the gain off in the loop to interrupt the build-up of ASE. Different regimes of operation are possible.

A pulse controlling block 900 delivers the pulses to control different stages in the embodiments presented above. As shown in FIG. 4, block 900 can pulsate the source, 10, along the line 90. This regime is not necessary all the time. In some regimes of operation of the embodiment in FIG. 4, the source 10 emits continuously, or when the source is swept, or when the photodetectors 41 and 41' are replaced with spectrometers, the source may also emit continuously.

Block 900 can also switch on and off the loops via the fast optical switches, 86 and 86', which can be amplitude modulators.

The loops can also be switched on and off by TTL pulses sent to the drivers, 29 and 29', along lines 88 and 88'.

Line 87, 87' 88, 88' are used when the optical amplifiers 39, 39' are fibre amplifiers. If the optical amplifiers are semiconductors, then in addition to the procedures above, they could also be switched on and off or the level of DC adjusted via lines 98 and 98'.

A trigger pulse is also sent in some operation conditions, to different demodulating units, such as 70 in FIG. 4, along line 89, with suitable delay to temporally gate the photodetected signal.

As shown in FIG. 12a, 12b, 13a, 13b, to perform such functions, pulse controlling block 900 is equipped with a pulse generator 105, which generates the pulse sent to the source 10 along line 90, suitably delayed in the delay block 106, and with suitable time durations, to control the other blocks in the embodiments disclosed above.

To avoid relaxation oscillations introduced by driving the optical modulators 22 and 22' or internal mode-locking effects when driving semiconductor optical amplifiers 39 and 39', it may be preferable to drive fast optical switches, 86 and 86'. The pulses sent to these blocks may be in synchronism with the pulse sent to the optical source, and of different durations, as explained below.

For further reduction of the ASE, optical filters 67 and 67' may also be introduced into the loops, to implement a trade-off between the depth resolution and number of round trips.

Pulsed Regime (i) single pulse, of duration less than the round trip time of light in the secondary loops, which is multiple times recirculated through the secondary loops. This regime could have applications in producing a very fast A-scan with no moving parts, in A-scan based OCT imaging and in fast sequential interrogation of sensors;

(ii) continuous regime, or using input pulses larger than the round trip time, with applications in 3D T-scan based OCT in 9.1., 9.2 and 13 and in simultaneous sensing as explained in 7.1-7.3 above;

(i) Single Pulse in the Recirculating Loops

FIG. 11 implements a regime of operation where a pulse of duration less than the round trip is multiple times recirculated through the two loops in the reference and in the object branches. According to FIG. 12a, a pulse is launched along line 90 towards the low coherence optical source 10. Let us say that the round trip is τ=50 ns. The duration of the pulse generated is τ' slightly smaller than τ, shown as τ'=τ/2 in FIG. 12a. At every recirculating time period, τ, another pulse is generated along the fibre 21 (and 21'). The period of pulses generated is Mτ, where M is the number of pulse recirculations. The outputs 21 and 21' consist in pulses of duration τ' repeated at the recirculation period τ.

Preferably, the broadband source 10 will be used to launch a pulse of sufficient high power to bring the amplifiers 39 and 39' in both loops to saturation. Then, with losses compensated, at each new τ interval, a new pulse is launched in each arm. Pairs of such pulses interfere in splitter 4 and the interference gate shifts progressively in depth at each new τ by $OPD_{rec}$. For instance, considering the round trip of the configurations in FIG. 11 of 50 ns, 100 pixels (steps) in depth will take 5 μs and 1000 pixels 50 μs. This means that an A-scan of 1000 pixels in depth is acquired in 50 μs, with $OPD_{rec} = l_c = 20$ μm, this means a depth range of 20 mm. There will be no decay of sensitivity like in the SD-OCT and dynamic focus is also possible, in principle by using a fast electrical controllable lens, 53, or any other focusing element within the interface optics 56 in FIG. 4 (not shown in the simplified diagram in FIG. 11). The method can ensure very fast depth scanning with no mechanical means. The depth is now coded in the arrival time of the pulses and therefore frequency shifters, 22 and 22' are not necessary.

By the end of the A-scan duration, the recirculation needs to be stopped. Therefore, the optical amplifiers 39 and 39' are switched off for a short while, τ", along lines 98 and 98', or equivalently, other lines could be used, such as 87 and 87' if amplitude modulators are used. To compensate for delay in the optics, the block 900 has to deliver these pulses with suitable delays $D_O$ and $D_R$, in respect to the launched pulse to the source, sent along line 90, as shown in FIG. 12b. The A-scan is made from the amplitude of interference during pulses in the signal 6 received with a repetition equal to the round trip. For quasi continuous operation, it is desirable that τ' approaches τ.

16.1. Applications
Sensing

The embodiment in FIG. 11 can be used for the same type of sensing applications as described above in conjunction with FIG. 1-4. The sensor could be placed in the main object sensing path or preferably in one of the recirculation path. In this case, the invention advantageously can be used to amplify by multiple recirculations, tiny variations of the optical path change in the sensing path by scanning the main optical path difference as explained above. The invention can also advantageously be used to amplify tiny frequency shifts by multiple recirculations, detected using a spectrum analyzer for the signal 6.

As a sensor placed in one of the recirculation path, a single track sensor, a scattering cell, a SER sensor, a Raman cell, a microfluidic device, a resonant whispering gallery, a Fibre Bragg Grating or any other type of sensor could be used as before.

For enhanced sensitivity, a "dummy" sensor can be placed in the other recirculating path, not subject to any chemical compound or signal, and OPD changes or frequency shifts are measured, where the differences are amplified by multiple recirculations.

Depth Resolved Scanning of Large Depth Objects

The method can have applications in the generation of a long A-scan, as required to scan the anterior chamber or even the whole eye. This is possible here as the method is advantageously compatible with dynamic focus, while SD-OCT methods are not. An electrical lens may be used to adjust the focus at the scanning rate, according to the example above, for 2 cm scanning range, in 50 μs. If the focus is slow, let us say that the focus requires 1 ms for 2 cm, then the optical recirculation duration τ can be increased to 1 μs. 1000 points now require 1 ms. As shown in FIG. 12a, the A-scan is built in synchronism on a scope with the trigger 89, after a delay $D_{ph}$ corresponding to the cumulated optical and electronic delays incurred up to the photodetection unit, 42 and demodulator unit 107, which deliver the A-scans, along line 108, for a duration $M\tau - \tau'$.

Tracking the Position of a Fast Moving Reflector

Tracking the axial position of the cornea leads to stabilization of the OCT images collected from the retina. In comparison to the method described before at 9.4. which required RF demodulation, here the position of the reflector or of the cornea is obtained from the number of recirculations, i.e. the method operates in time. The succession of control pulses is described in FIG. 12b. One of the multiple coherence gate windows within an A-scan coincides with the peak of the reflection from the cornea or any surface being tracked axially. The resolution of the method is given by the recirculation time, τ. A trigger Schmidt, 107, is switched on with the launched pulse for the source, delayed by $D_{ph}$ to compensate for the optical and electronic delay, and is switched off with the pulse from the photodetector signal, at the $D_{axial}$ instant. In this way, the axial distance of the reflector is converted into the duration of output pulses, $D_{axial}$, as shown by the signal 108. An integrator of the photodetected signal can provide a magnitude proportional to the pulse width so generated. This can subsequently be used to control the OPD value in real time in an OCT system used to image the retina. For the example given, for M=100 points at 50 ns, the update could happen as fast as 5 microseconds for a tracking range of 2 mm, considering a coherence length of 20 microns.

OTDR.

Multiple reflections along a fibre could be located using the same principle. The advantage of using two loops, one in each interferometer arm, is that dynamic dispersion compensation takes place. For instance, the extra delay $OPD_{rec}$ can be provided by a fibre, δl, made from the same material of the fibre communication link, or hundred of miles. If let us say the fibre δl, is 10 cm, then with N=1000 round trips, 10 m can be investigated. In this case, it would be desirable to lengthen the coherence length of the source to δl=10 cm. Then, the small length piece of fibre is removed and replaced with a fibre of length δl=10 m. Now the system will provide 1000 points at 10 m each, so 10 km can be investigated. In this case, it would be desirable to lengthen the coherence length of the source to δl=10 m. The coherence length can be adjusted by either changing the optical source or by using spectral filters. This demonstrate the scalability of the method. In prior art implementations, dispersion of fibre prevented OTDR instrumentation from using interference. Because at each round trip, a new piece of path length is added, similar to that explored in axial distance along the fibre link, dynamic compensation results. The reflectivity profile is built according to the description in FIG. 12a.

(ii) Pulses Longer than the Round Trip Time

In order to improve the uniformity of multiple frequency signals generated by the embodiment in FIG. 4, a pulsed operation regime can be employed as described in FIG. 13a. Let us say that we wanted to generate N=5 equal amplitude signals at least. A pulse of duration τ', slightly less than the round trip time, τ, is launched by the block 105 into the low coherence source 10, this has power P at the optical amplifier input, which is less than 5 times the saturation power of the optical amplifier, $P_s$, of the amplifiers 39 and 39'. The loops are open for a duration T=2Nτ, with the example above of τ=50 ns, this gives T=500 ns. The pulses sent from the block 900 are also of the same repetition rate, T. At every τ, the power in the loops goes up by P, until it reaches saturation and then decrease to zero by the end of the period T. In this time, out of the recirculation loops, along fibres 21 and 21', pulses carrying different frequency shifts in a following number will result:

5 pulses for each of m=1, 2, 3, 4 and 5 frequency shifts are obtained, at the output of the two arms recirculating loops. When beating the signals from the two arms in the balance unit 42, the photodetected signal pulsates at ΔF, 2ΔF, 3ΔF, 4ΔF and 5ΔF. They will all have equal intensities because signals contributing to these beatings will occupy half of the period T, ie they will all have an average power of 0.5P in T.

There will also be 4 pulses contributing to 6ΔF, 3 pulses contributing to 7ΔF, 2 pulses contributing to 8ΔF and one pulse contributing to 9ΔF. No more recirculations will take place as the loop will be switched off for a short duration, τ", by the end of the T period. Only channels from 1 to 5 multiple carriers will be used, as the intensity of the others decreases with the multiplicity order to 4/10, 3/10, 2/10 and 1/10 of P at the amplifier input. Because the power is kept low initially to avoid saturation, optical amplifiers 39 may be placed after the recirculation loops, in fibres 31a and 31a' in FIG. 4.

FIG. 13b describes another possibility, which is a combination of (i) and (ii) above. The pulse emitted from the source is less than the round trip time, however in the secondary loops, power builds up at every recirculation, as another pulse comes from the source. Delays are required to suitably open the loops when the pulses reach the respective elements, optical switches 86 and 86', modulator drivers 29 and 29' and amplifiers 39 and 39'. The loops are switched on and off at the round trip time, τ, therefore no ASE is built up. Pulses accumulate and reach saturation. As explained in FIG. 13a, this can be stopped by switching off the loops and the input optical powers. Combination of principles described in FIGS. 13a and 13b can be devised.

The foregoing description has been presented for the sake of illustration and description only. As such, it is not intended to be exhaustive or to limit the invention to the precise form disclosed. For example, reference was primarily made to measurements in transmission and imaging in reflection, however measurements in reflection and imaging in transmission could equally be performed. Several examples have been given on using the multipath interferometer 100 in time domain OCT and spectral domain OCT. These are not exhaustive, have been presented as a matter of example and modifications and variations are possible in light of the above teaching which are considered to be within the scope of the present invention. Thus, it is to be understood that the claims appended hereto are intended to cover such modifications and variations which fall within the true scope of the invention.

Other modifications and alterations may be used in the design and manufacture of the apparatus of the present invention and in the application of the methods disclosed without departing from the spirit and scope of the accompanying claims.

Variations include the grouping of recirculation optical loops with a main loop, via a splitter or two splitters between an optical sources and photodetection outputs.

Variations may include the grouping of optical devices in the recirculating loops, such as optical modulators (at least one of the following: frequency shifter, amplitude modulator, phase modulator, polarization modulator, spectral scanning delay line) with optical amplifiers.

The optical source can be pulsed with pulses of width less or larger than the recirculating time of the optical wave through each of the recirculation loop. The optical source may also be continuous.

Variations may also include the operation of the invention in sensing or OCT imaging.

Variations include the photodetection unit which may consist of at least one photodetector, and/or two photodetectors whose electrical signals are subtracted one from the other in a balance detection configuration.

The frequency shifting means may consist in a single frequency shifter excited at $\Delta F$ and placed in any of the two recirculating paths. Alternatively, the frequency shifting means may consist in an object frequency shifter in the recirculating object path excited at a frequency $F_O$ and a reference frequency shifter in the recirculating reference path excited at a frequency $F_R$ and where the difference or sum of the frequency $F_O$ and of the frequency $F_R$ determines the interference frequency shift $\Delta F$.

In the above, selection of the difference of frequencies, $|F_O - F_R|$ is preferred for allowing the photodetector unit 43 work on lower frequency values. However, in some applications, it may be desirable to operate on the sum of the two frequencies, with $\Delta F = F_O + F_R$.

A sensor may be placed within the main object sensing path and where the sensor consists in a 1 by N tree terminated by a N by 1 tree and where the lengths of paths between the two trees represent sensing paths and are of different length, varying by an increment d and where the $OPD_{rec}$ is adjusted to match d.

The invention claimed is:
1. A multipath interferometer, having
a first main splitter for splitting an input beam from an optical source into an object beam along a main object path and into a reference beam along a main reference path having a main optical path difference $OPD_{main}$ between the main object path and main reference path;
a recirculating object path split off the main object path, and a recirculating reference path split off the main reference path
wherein a recirculating optical path difference between the recirculating object path and the recirculating reference path is $OPD_{rec}$;
and independent optical path adjusting means for adjusting the main optical path difference $OPD_{main}$ independently from the recirculating optical path difference $OPD_{rec}$ and where the multipath interferometer drives a photodetection unit.
2. A multipath path interferometer according to claim 1:
wherein the object beam from the first main splitter is launched into the first input of a second object splitter,
one of the output feeds of the second object splitter follows the main object path to a third object splitter;
one of the output feeds of the third object splitter feeds the main object path towards a first input of a fourth main splitter terminated on a photodetecting unit;
the path from the first main splitter via the third object splitter to the fourth main splitter defines a main object path of optical length $D_O$;
where the second output of the third object splitter launches recirculating beam along the recirculating object path towards the second input of the second object splitter, where light is reinjected back into the main object path, and where the path length of the recirculating object beam starts from the third object splitter and extends via a second input of the second object splitter and the main object path up to the third object splitter and is of optical length $L_O$;
the path along the main object path not shared with the object recirculating path defines a main object sensing path,
wherein the reference beam from the first main splitter is launched into the first input of a second reference splitter,
one of the output feeds of the second reference splitter follows the main reference path to a third reference splitter;
one of the output feeds of the third reference splitter feeds the main reference path towards a first input of the fourth main splitter;
the path from the main reference splitter via the third reference splitter to the fourth main splitter defines a main reference path of optical length $D_R$;
where the second output of the third reference splitter launches recirculating beam along the recirculating reference path towards the second input of the second reference splitter, where light is reinjected back into the main reference path, and where the path length of the recirculating object beam starts from the third reference splitter and extends via a second input of the second reference splitter and the main reference path up to the third reference splitter and is of optical length $L_R$; and
the object beam launched into the fourth splitter consists in a superposition of the main object beam delayed by $D_O$ and replicas of the object beam delayed by $D_O + mL_O$
the reference beam launched into the fourth main splitter consists in a superposition of the main reference beam delayed by $D_R$ and replicas of the reference beam delayed by $D_R + mL_R$ with m the number of round trips of beams through the recirculating paths.
3. A multipath path interferometer according to claim 1, wherein
the object beam is launched into the first input of a second object splitter, one of the outputs of the second object splitter feeds the main object path towards a first input of a fourth main splitter terminated on a photodetecting unit, the path from the first main splitter via the second object splitter until the fourth main splitter defines a main object path of optical length $D_O$, and the second output of the second object splitter launches a recirculating beam along a recirculating object path of optical length $L_O$ towards the second input of the second object splitter, where light is reinjected back into the main object path, and the path along the main object path not shared with the object recirculating path defines a main object sensing path, the reference beam is launched into a first input of a second reference splitter, one of the outputs of the second reference splitter feeds the main reference path towards the second input of the fourth main splitter and where the path from the first main splitter via the second reference splitter till the fourth main splitter defines a main reference path of optical length $D_R$, and the second output of the second reference splitter launches a recirculating beam along a recirculating reference path of optical length $L_R$, towards the second input of the second reference splitter, where light is reinjected back into the main reference path, and the object beam launched into the fourth main splitter consists in a superposition of the main object beam delayed by $D_O$ and replicas of the object beam delayed by $D_O + mL_O$ the reference beam launched into the fourth main splitter consists in a superposition of the main reference beam delayed by $D_R$ and replicas of the reference beam delayed by $D_R + mL_R$ with m the number of round trips of beams through the recirculating paths.

4. A multipath interferometer according to claim 1 further comprising at least one optical amplifier in the recirculating object path not shared with main object path and at least one optical amplifier in the recirculating reference path not shared with the main reference path.

5. A multipath interferometer according claim 1 further comprising a frequency shifting means arranged to shift the frequency of the light in the recirculating object path after m passes in respect to the frequency of the light in the recirculating reference path after the same number of m passes by a multiple m of an interference frequency shift $\Delta F$.

6. A multipath interferometer according to claim 5 where the photodetection unit outputs a signal $s_m$ of frequency $m\Delta F$ when $OPD_{main} + mOPD_{rec}$ is substantially within the coherence length of the light.

7. A multipath interferometer according to claim 1 further comprising at least one fast optical switch in the recirculating object path not shared with main object path and at least one fast optical switch in the recirculating reference path not shared with the main reference path which can be used to controllably stop the wave recirculation.

8. A multipath interferometer according to claim 1, further comprising a multi-channel demodulator of the signal provided by the said photodetection unit to separate and process m interference signal components $s_m$ parts thereof, into m channels.

9. A multipass interferometer according to claim 8, wherein each channel of the multi-channel demodulator contains a band pass filter tuned on a multiple of the interference frequency shift, $\Delta F$, provided by said means of frequency shifting and each channel provides an output signal $O_m$.

10. A multipass interferometer according to claim 9 wherein the output signal Om of the multi-channel demodulator is the strength of the signal $s_m$, represented as an amplitude $A_m$.

11. A multichannel filter according to claim 9 where the output signal Om of the demodulator is the phase of the m-th component, $s_m$, $\Phi_m$.

12. A multipath interferometer according to claim 1 wherein the main object path further comprises a fifth object splitter placed in the main object sensing path, which sends light towards an object to be investigated in reflection and collects backscattered light and redirects it towards the fourth splitter.

13. A multipath interferometer according to claim 12 where a transverse scanner and interface optics are incorporated between the fifth object splitter and the object to scan light over the said object.

14. A multipath interferometer according to claim 13, wherein a mapping block produces a C-scan$_m$ map of $A_m$ values versus the transversal position of the object beam determined by the said transverse scanner and where a 3D voxel is assembled by the multi-channel demodulator using several C-scan$_m$ maps separated by axial optical distances determined by $OPD_{rec}$.

15. A multipath interferometer according to claim 1 where the means for frequency shifting use one or more Bragg cells to shift the optical frequency by $F_p$ and the frequency $\Delta F$ is obtained as any possibility of $$\Delta F = \left| \Delta F = \sum_p (\pm F_p) \right|.$$

16. A multipath interferometer according to claim 1 further comprising a means for frequency shifting use spectral scanning delay lines consisting in at least a dispersing element, a converging element and a galvo-scanner wherein the interference frequency shift may be adjusted by moving the incidence of the beam away from the pivot of the said galvo-scanner.

17. A multiple path interferometer according to claim 1, where the said optical source is a low coherence source, with a spectrum bandwidth sufficiently wide to determine a coherence length much shorter than a fraction of the penetration depth range of time domain OCT in the object.

18. A multiple path interferometer according to claim 1, where the said optical source is a high coherence swept source, where sweeping takes place in a bandwidth sufficiently wide to determine a swept source depth resolution OCT much shorter than a fraction of the penetration depth range of time domain OCT in the object, and its linewidth is such as to determine a swept source depth range comparable to the object thickness.

19. A multiple path interferometer according to claim 1 where the photodetection unit uses at least one spectrometer equipped with a photodetection array and where the signal delivered by the array is Fourier transformed to deliver an A-scan.

20. A multiple path interferometer according to claim 1 where complex Fourier transformations are evaluated based on the modulation with the signal of frequency $m\Delta F$ in each channel m.

21. A multiple path interferometer according to claim 1, where one or more of the following: an optical source, a driver of a frequency shifter, an optical amplifier, a fast optical switch are pulsed and the pulses sent to any two of the said optical source, driver of the frequency shifter, optical amplifier, fast optical switch are synchronized.

22. A method of multipath interferometry comprising:

splitting an input beam from an optical source into an object beam along a main object path and a reference beam along a main reference path having a main optical path difference $OPD_{main}$ between the main object path and main reference path;

splitting light off the main object path along a recirculating object path;

splitting light off the main reference path along a recirculating reference path wherein a recirculating optical path difference between the recirculating object path and the recirculating reference path is $OPD_{rec}$;

adjusting the main optical path difference $OPD_{main}$ independently from the recirculating optical path difference $OPD_{rec}$ to produce an overall $OPD=OPD_{main} \pm mOPD_{rec}$ between the object beam and reference beam suffering m recirculations and analyzing the interference of the recirculated object beam and recirculated reference beam.

23. A method according to claim 22 wherein further comprising optical amplification in the recirculation paths.

24. A method according to claim 22 wherein further comprising shifting the frequency of light in the recirculating object path after m passes in respect to the frequency of light in the recirculating reference path after the same number of m passes by an integer m multiple of an interference frequency shift $\Delta F$ and wherein the said process of photodetecting light provides simultaneously working OCT channels, a channel for each photodetected signal $s_m$, resulting from interference of optical beams traversing optical path difference lengths which correspond to values when $OPD_{main}+mOPD_{rec}$ is substantially zero, where $s_m$ pulsate at multiple of the interference frequency shift $\Delta F$, with m equal to zero or any integer and where the values of $OPD_{main}$ and of the $OPD_{rec}$ are adjusted independently of each other in order to match the start of OPD value from $OPD_{main}$ and subsequent OPD values in steps of $OPD_{rec}$.

25. A method according to claim 22 including dynamic dispersion compensation by adjusting the $OPD_{rec}$ to be determined by a slab similar in optical properties to the said object with an optical thickness given by the differential depth at which multiple depth resolved measurements are to be taken from the object, and where the $OPD_{main}$ is adjusted to zero up to a reference depth range of interest in the object wherefrom depth scanning starts in steps of $OPD_{rec}$ for the object evaluated in transmission and in steps $OPD_{rec}/2$ if the object is evaluated in reflection.

26. A method of multipath interferometry according to claim 22 where a multipath sensor with multiple sensing paths is inserted into the object path and where the said optical source is a low coherent source and where the said multipath sensing paths are scanned simultaneously by scanning the $OPD_{main}$ and the length of each individual sensing path is evaluated from the temporal delay of the rectified $m\Delta F$ signal in each said channel of signal $s_m$ in respect to the moment of starting scanning of the $OPD_{main}$.

27. A method of multipath interferometry according to claim 22 where the object beam is scanned in 2D to produce a C-scan and where the multiple signals $s_m$ are used to assemble OCT C-scans at different axial positions in the object starting from a depth determined by $OPD_{main}$ and separated by axial distances determined by $OPD_{rec}$.

28. A method of multipath interferometry according to claim claim 22 where the object beam is scanned in 1D to produce a T-scan and where the multiple signals $s_m$ are used to assemble an OCT B-scan from the object from multiple T-scans separated by axial distances determined by $OPD_{rec}$ and starting from a depth determined by $OPD_{main}$.

29. A method according to claim 22 wherein further comprising pulsating the said optical source for a duration $\tau$ less than the round trip $\tau$ defined as the time for the electromagnetic wave to travel along the recirculating path once, with a period T and assembling an interference signal formed from many m temporal replicas sequentially produced in steps $\tau$ for a duration T due to m round trips through the recirculating loops.

30. A method according to claim 22 where the said analyzing the interference involves photodetection.

31. A method according to claim 22 where the said analyzing the interference involves spectral decomposition.

32. A method according to claim 22 wherein the said optical source is a narrow band swept source.

33. A method according to claim 22 which is used in sensing or molecular recognition of a compound by placing it in one of the recirculation loops and using amplification of frequency shifts due to the compound in multiple round trips of the recirculation beam traversing the compound.

34. A method according to claim 22 which is used in sensing or molecular recognition of a compound by placing it in one of the recirculation loops and using amplification of optical path disturbance due to the compound in multiple round trips of the recirculation beam traversing the compound.

35. A method according to claim 22 wherein only one pulse, of a given delay at a time is present in the recirculation paths.

36. A method according to claim 22 wherein more than one pulse at a time is present in the recirculation paths where each pulse corresponds to a given optical delay.

* * * * *